US006486305B1

(12) United States Patent
Peltz et al.

(10) Patent No.: US 6,486,305 B1
(45) Date of Patent: Nov. 26, 2002

(54) METHOD OF MODULATING THE EFFICIENCY OF TRANSLATION TERMINATION AND DEGRADATION OF ABERRANT MRNA INVOLVING A SURVEILLANCE COMPLEX COMPRISING HUMAN UPF1P, EUCARYOTIC RELEASE FACTOR 1 AND EUCARYOTIC RELEASE FACTOR 3

(76) Inventors: Stuart Peltz, 67 Castle Pointe Blvd., Piscataway, NJ (US) 08854; Kevin Czaplinski, 115 Hollywood Ave., Somerset, NJ (US) 08873; Youmin Weng, 2 Indian Spring Rd., Cranford, NJ (US) 07016

(*) Notice: Subject to any disclaimer, the term of this patent is extended or adjusted under 35 U.S.C. 154(b) by 0 days.

(21) Appl. No.: 09/639,987

(22) Filed: Aug. 16, 2000

Related U.S. Application Data

(62) Division of application No. 09/086,260, filed on May 28, 1998, now abandoned.

(51) Int. Cl.[7] .............................. A23J 1/00; C07K 1/00; A61K 38/16; C12P 21/06; C12N 15/63
(52) U.S. Cl. ...................... 530/412; 435/69.1; 435/455; 530/350; 530/358
(58) Field of Search .................. 435/4, 6, 455, 435/91.31, 69.1; 530/350, 412, 358, 820; 536/24.5

(56) References Cited

U.S. PATENT DOCUMENTS

| 5,641,627 A | 6/1997 | Moehle |
| 5,679,566 A | 10/1997 | He et al. |
| 5,840,702 A | 11/1998 | Bedwell |
| 5,874,231 A | 2/1999 | Sonenberg et al. |
| 5,994,119 A | 11/1999 | Dietz |

FOREIGN PATENT DOCUMENTS

| WO | WO 97/12617 | 4/1997 |
| WO | WO 9734611 | 9/1997 |
| WO | WO 97/40855 | 11/1997 |

OTHER PUBLICATIONS

Applequist et al. Nucleic Acids Res., vol. 24, No. 4, pp. 814–821, 1997.*
Atkin et al. J. Biol. Chem., vol. 272, No. 35, pp. 22, 163–22, 172, 1997.*
Drugeon et al. Nucleic Acids Res., vol. 25, pp. 2254–2258, 1997.*
Perlick et al. Proc. Natl. Acad. Sci., USA, vol. 93, pp. 10,928–10,932, 1996.*
Frolova et al. RNA 2:33–341 (1996).
Branch TIBS 23: 45–50 (Feb. 1998), (published after filing of parent application).
Czaplinski, et al. RNA 1:610–623 (1995).
Czaplinski, et al. Bioessays 21:685–696 (1999).
Czaplkinski, et al. Genes & Development 12:1665–1677 (Jun. 1998).
Andjelkovic, et al. Medline Abstract 2191 (EMBOJ. 15:7156–7167 (1996).
Peltz, et al. Progress in Nucleic Acid Research and Molecular Biology 47:271–298 (1994).
Weng, et al. Molecular and Cellular Biology 16:5477 (1996).
Biswas, et al. Biochem and Biophys Research Communications 206:850–856 (1995).
Howard, et al. Nature Medicine 2:467–469 (1996).

* cited by examiner

Primary Examiner—Sean McCarry
Assistant Examiner—Jane Zara
(74) Attorney, Agent, or Firm—Lyon & Lyon LLP

(57) ABSTRACT

This invention provides a method of modulating translation termination efficiency of mRNA and/or promoting degradation of aberrant transcripts. Also, this invention provides a method of screening for a drug active involved in enhancing translation termination and a method for identifying a disease state involving defective the protein complex.

This invention provides a purified complex comprising an amount of a human Upf1p protein, a peptidyl eucaryotic release factor 1 (eRF1) and a peptidyl eucaryotic release factor 3 (eRF3) effective to modulate translation termination. Further, this invention provides an expression vector which comprises a nucleic acid encoding a human Upf1p protein, a peptidyl eucaryotic release factor 1 (eRF1) and a peptidyl eucaryotic release factor 3 (eRF3) operably linked to a regulatory element.

This invention provides an antibody which binds to the complex comprising an amount of a human Upf1p protein, a peptidyl eucaryotic release factor 1 (eRF1) and a peptidyl eucaryotic release factor 3 (eRF3) effective to modulate translation termination. This invention provides an agent which inhibits or modulates the binding of human Upf1p to eRF1 or eRF3 The agent may inhibit or facilitate the binding of human Upf1p to eRF1 or eRF3.

3 Claims, 11 Drawing Sheets

Fig. 1
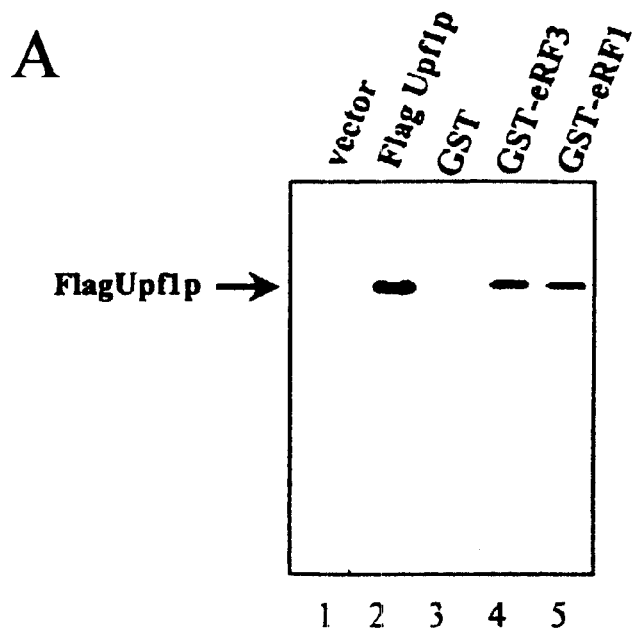
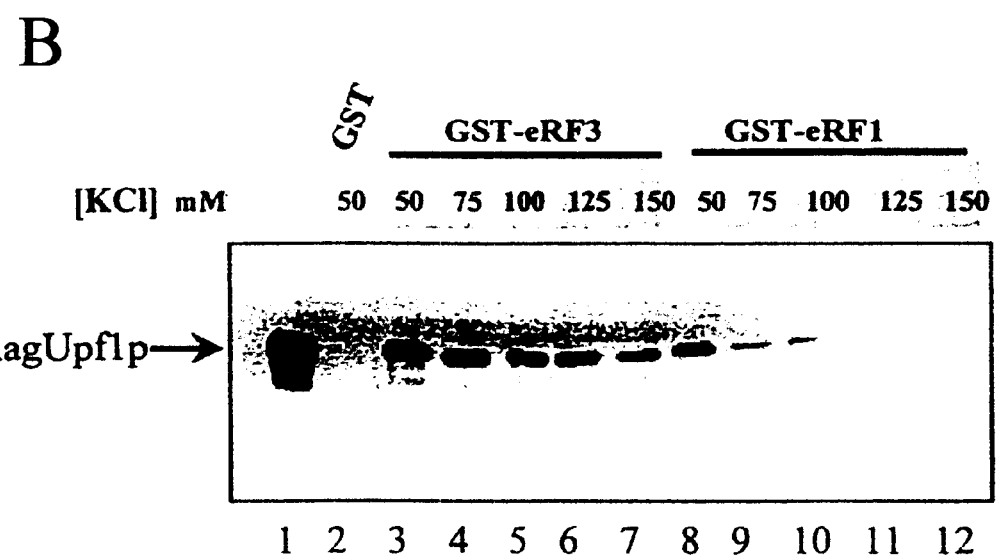

Fig. 3
A
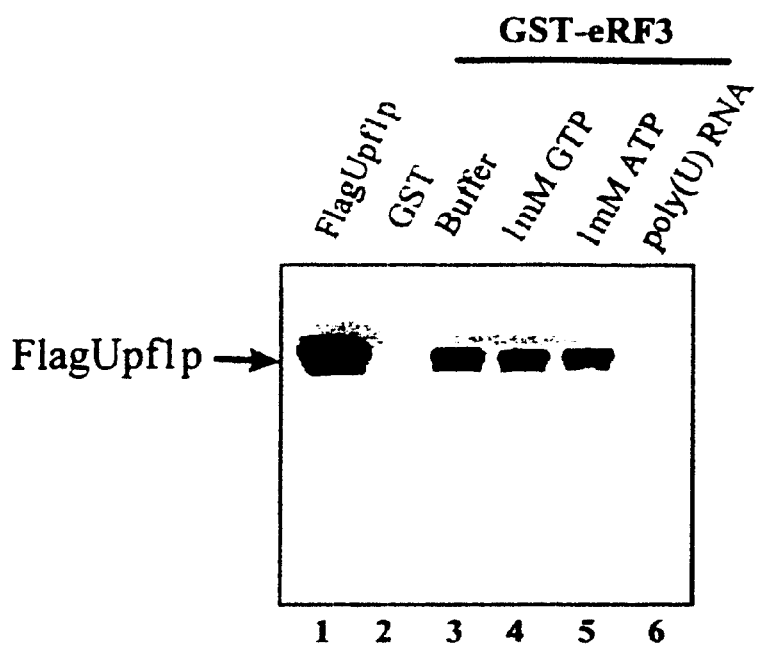
B
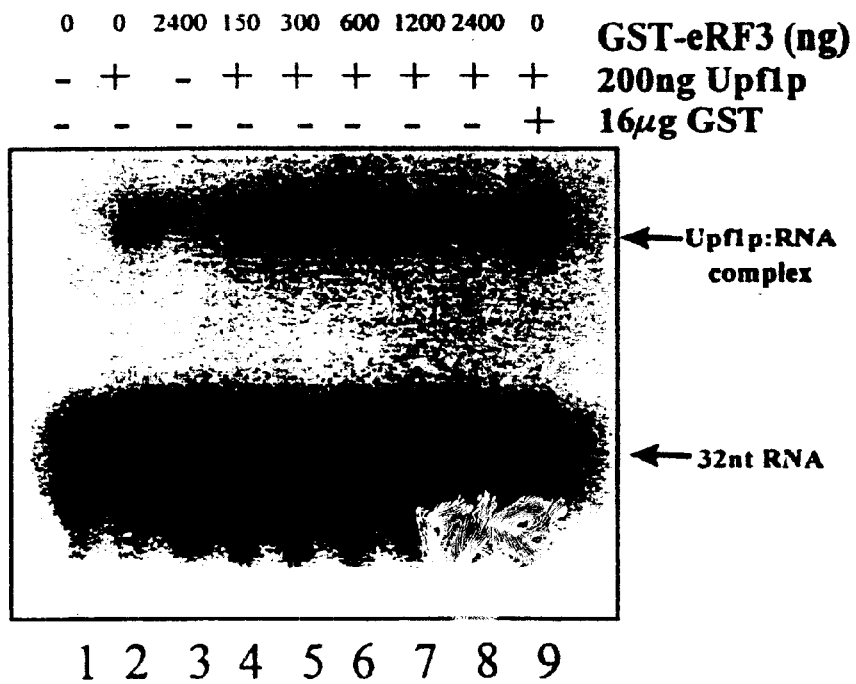

Fig. 5
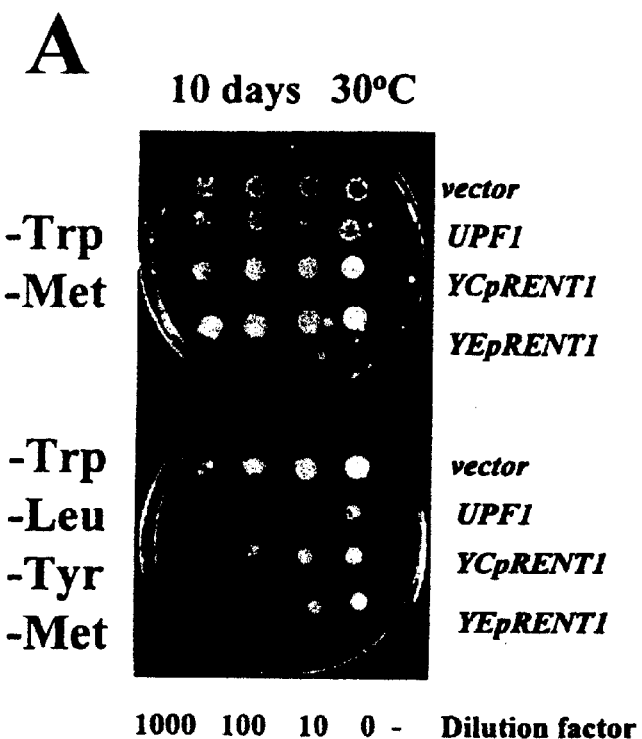
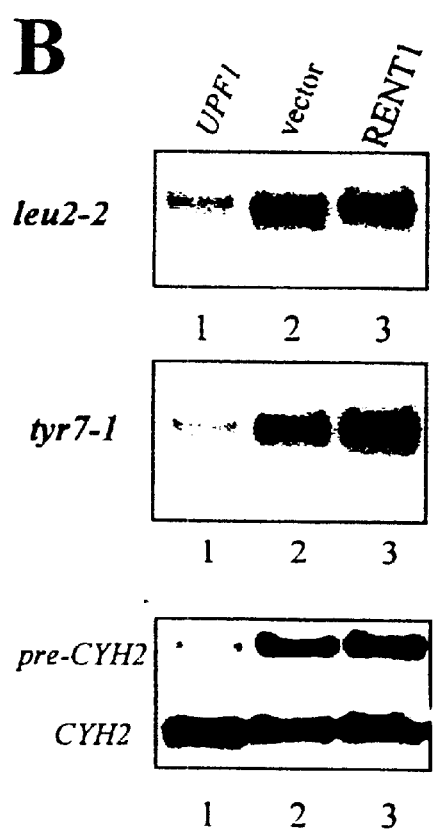

*Fig. 11*
STRAIN  WT  *upf3Δ*
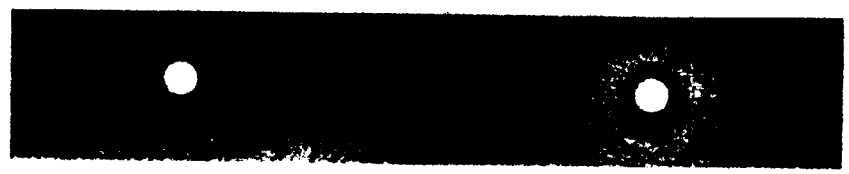

US 6,486,305 B1

METHOD OF MODULATING THE EFFICIENCY OF TRANSLATION TERMINATION AND DEGRADATION OF ABERRANT MRNA INVOLVING A SURVEILLANCE COMPLEX COMPRISING HUMAN UPF1P, EUCARYOTIC RELEASE FACTOR 1 AND EUCARYOTIC RELEASE FACTOR 3

This Application is a Divisional of application patent Ser. No. 09/086,260 filed May 28, 1998 now abandoned.

GOVERNMENT RIGHTS CLAUSE

The research leading to the present invention was supported, at least in part, by a grant from The National Institutes of Health (GM48631-01). Accordingly, the Government may have certain rights in the invention.

FIELD OF THE INVENTION

The present invention relates to a multiprotein surveillance complex comprising human Upf1p eucaryotic Release Factor 1 and eucaryotic Release Factor 3 which is involved in modulation of the efficiency of translation termination and degradation of aberrant mRNA. Identification of this complex provides an in vitro assay system for identifying agents that: affect the functional activity of mRNAs by altering frameshift frequency; permit monitoring of a termination event; promote degradation of aberrant transcripts; provide modulators (inhibitors/stimulators) of peptidyl transferase activity during initiation, elongation, termination and mRNA degradation of translation. Such agents which may be antagonists or agonists, are useful for screening, and diagnostic purposes, and as therapeutics for diseases or conditions which are a result of, or cause, premature translation.

BACKGROUND OF THE INVENTION

Recent studies have demonstrated that cells have evolved elaborate mechanisms to rid themselves of aberrant proteins and transcripts that can dominantly interfere with their normal functioning (reviewed in Gottesman et al. 1997, He et al. 1993, Jacobson and Peltz 1996, Ruiz-Echevarria et al. 1996, Suzuki et al. 1997, Weng et al. 1997, Maquat, 1995, Pulak and Anderson, 1993). Such pathways can be viewed both as regulators of gene expression and as sensors for inappropriate polypeptide synthesis. The nonsense-mediated mRNA decay pathway (NMD) is an example of a translation termination surveillance pathway, since it eliminates aberrant mRNAs that contain nonsense mutations within the protein coding region (Gottesman et al. 1997, He et al. 1993, Jacobson and Peltz, 1996, Ruiz-Echevarria et al. 1996, Suzuki et al. 1997, Weng et al. 1997, Pulak and Anderson, 1993, Caponigro and Parker, 1996, Maquat, 1995). The NMD pathway has been observed to function in all eucaryotic systems examined so far and appears to have evolved to ensure that termination of translation occurs at the appropriate codon within the transcript. Transcripts containing premature nonsense codons are rapidly degraded, thus preventing synthesis of incomplete and potentially deleterious proteins. There are well over two hundred genetic disorders which can result from premature translation termination (McKusick, 1994).

The proteins involved in promoting NMD have been investigated in C. elegans mammalian cells and in the yeast Saccharomyces cerevisiae. Three factors involved in NMD have been identified in yeast. Mutations in the UPF1, UPF2, and UPF3 genes were shown to selectively stabilize mRNAs containing early nonsense mutations without affecting the decay rate of most wild-type mRNAs (He and Jacobson 1995, Lee and Culbertson 1995, Leeds et al. 1992, Leeds et al. 1991, Cui et al. 1995). Recent results indicate that the Upf1p, Upf2p and Upf3p interact and form a complex (He and Jacobson 1995, He et al. 1997, Weng et al. 1996b). In C. elegans, seven smg alleles have been identified which result in an increased abundance of nonsense-containing transcripts (Pulak and Anderson, 1993). A human homologue of the UPF1 gene, called RENT1 or HUPF 1, has been identified, indicating that NMD is an evolutionarily conserved pathway (Perlick et al. 1996, Applequist et al. 1997).

Although the cellular compartment in which NMD occurs in mammalian cells is controversial (Weng et al., 1997; Maquat, 1995; Zhang and Maquat 1997), it appears that in yeast, however, NMD occurs in the cytoplasm when the transcript is associated with ribosomes. Results supporting this conclusion are the following; 1) nonsense-containing and intron-containing RNAs that are substrates of the NMD pathway in yeast become polysome-associated and are stabilized in the presence of the translation elongation inhibitor cycloheximide (Zhang et al. 1997). The polysome associated RNAs, however, regain their normal rapid decay kinetics when the drug is washed out of the growth medium and translation resumes (Zhang et al., 1997); 2) Upf1p, Upf2p and Upf3p have been shown to be associated with polysomes (Peltz et al., 1993a, 1994; Atkin et al., 1995; Atkin et al., 1997); 3) as revealed by fluorescent in situ hybridization analysis, the cytoplasmic abundance of an intron-containing LacZ reporter RNA containing mutations in the 5' splice site or branch point was dramatically reduced in UPF1$^+$ strain but increased in cytoplasmic abundance in upf1Δ cells (Long et al., 1995); 4) NMD can be prevented by nonsense-suppressing tRNAs (Losson and Lacroute, 1979; Gozalbo and Hohmann, 1990; Belgrader et al., 1993); 5) the NMD pathway is functional only after at least one translation initiation/termination cycle has been completed (Ruiz-Echevarria and Peltz, 1996; Ruiz-Echevarria et al., 1998; Zhang and Maquat, 1997). Furthermore, a translation reinitiation event can prevent activation of the NMD pathway (Ruiz-Echevarria and Peltz, 1996; Ruiz-Echevarria et al., 1998; Zhang and Maquat, 1997). Taken together, these results indicate that the NMD pathway in yeast is a cytoplasmic and translation-dependent event. The rent1/hupf1 protein is also predominantly cytoplasmic (Applequist et al. 1997)

The yeast UPF1 gene and its protein product have been the most extensively investigated factor of the putative surveillance complex (Czaplinski et al. 1995, Weng et al. 1996a,b, Weng et al., 1998, Altamura et al. 1992, Cui et al. 1996, Koonin, 1992, Leeds et al. 1992, Atkin et al. 1995, 1997). The Upf1p contains a cysteine- and histidine-rich region near its amino terminus and all the motifs required to be a member of the superfamily group I helicases. The yeast Upf1p has been purified and demonstrates RNA binding and RNA-dependent ATPase and RNA helicase activities (Czaplinski et al. 1995, Weng et al. 1996a,b). Disruption of the UPF1 gene results in stabilization of nonsense-containing mRNAs and suppression of certain nonsense alleles (Leeds et al. 1991, Cui et al. 1995, Czaplinski et al. 1995, Weng et al. 1996a; Weng et al. 1996b).

SUMMARY OF THE INVENTION

The ability to modulate translation termination has important implications for treating diseases associated with nonsense mutations. As with any biological system, there will be a small amount of suppression of a nonsense mutation, resulting in expression of a full length protein (which may or may not include an amino acid substitution or deletion). In the natural state, such low quantities of full length protein are produced that pathology results. However, by stabilizing the nonsense mRNA, the likelihood of "read-through" transcripts is dramatically increased, and may allow for enough expression of the protein to overcome the pathological phenotype.

The nonsense-mediated mRNA decay pathway is an example of an evolutionarily conserved surveillance pathway that rids the cell of transcripts that contain nonsense mutations. The product of the UPF1 gene is a necessary component of the putative surveillance complex that recognizes and degrades aberrant mRNAs. The results presented here demonstrate that the yeast and human forms of the Upf1p interact with both eucaryotic translation termination factors eRF1 and eRF3. Consistent with Upf1p interacting with the eRFs, the Upf1p is found in the prion-like aggregates that contain eRF1 and eRF3 observed in yeast [PSI$^+$] strains. These results indicate that interaction of the Upf1p with the peptidyl release factors is a key event in the assembly of the putative surveillance complex that enhances translation termination monitors whether termination has occurred prematurely and promotes degradation aberrant transcripts.

This invention provides an isolated complex comprising a human Upf1p protein, a peptidyl eucaryotic release factor 1 (eRF1) and a peptidyl eucaryotic release factor 3 (eRF3), wherein the complex is effective to modulate peptidyl transferase activity. In one embodiment, this invention further comprises a human Upf3p and Upf2p.

This invention provides an agent which binds to the complex comprising an amount of a human Upf1p protein, a peptidyl eucaryotic release factor 1 (eRF 1) and a peptidyl eucaryotic release factor 3 (eRF3) effective to modulate translation termination. This invention provides an agent which binds to the complex of claim 1, wherein the agent inhibits ATPase of Upf1p; GTPase activity of eRF1 or eRF3; or RNA binding to a ribosome. This invention provides an agent which inhibits or modulates the binding of human Upf1p to eRF 1, or eRF3 or eRF1 or eRF3 to Upf1p. This invention provides an agent which inhibits or modulates the binding of human Upf3p to eRF1, or eRF3 or eRF1 or eRF3 to Upf3p. This invention provides an agent which facilitates the binding of human Upf1p to eRF1 or eRF3; or eRF3 or eRF1 or eRF3 to Upf1p. This invention provides an agent which facilitates the binding of human Upf3p to eRF1 or eRF3; or eRF3 or eRF1 or eRF3 to Upf1p. This invention provides an agent which modulates the binding of human Upf1p, eRF1 or eRF3 to a ribosome.

This invention provides a method of modulating peptidyl transferase activity during translation, comprising contacting a cell with the complex in an amount effective to facilitate translation termination, thereby modulating the peptidyl transferase activity.

This invention provides a method of modulating peptidyl transferase activity during translation, comprising contacting a cell with the agent, in an amount effective to suppress non-sense translation termination, thereby modulating the peptidyl transferase activity. The peptidyl transferase activity during translation occurs during initiation, elongation, termination and degradation of mRNA.

This invention provides a method of modulating the efficiency of translation termination of mRNA at a non-sense codon and/or promoting degradation of abberant transcripts, comprising contacting a cell with the agent, in an amount effective to inhibit the binding of human Upf1p to eRF1, or eRF3; or eRF1 or eRF3 to Upf1, thereby modulating the efficiency of translation termination of mRNA at a non-sense codon and/or promoting degradation of abberant transcripts.

This invention provides a method of modulating the efficiency of translation termination of mRNA at a non-sense codon and/or promoting degradation of abberant transcripts, comprising contacting a cell with an agent, which inhibits the ATPase/helicase activity of Upf1p; the GTPase activity of eRF1 or eRF3, or binding of RNA to a ribosome, thereby modulating the efficiency of translation termination of mRNA at a non-sense codon and/or promoting degradation of abberant transcripts.

This invention provides a method of screening for a drug involved in peptidyl transferase activity during translation comprising: a) contacting cells with a candidate drug; and b) assaying for modulation of the complex, wherein a drug that modulates the complex is involved in peptidyl transferase activity or enhancing translation termination.

This invention provides a method of screening for a drug involved in enhancing translation termination comprising: a) incubating the drug and the complex; and b) measuring the effect on non-sense suppression, thereby screening for a drug involved in enhancing translation termination. The assays may be a RNA or NTPase assays, such as ATPase or GTPase.

This invention provides a method of modulating the efficiency of translation termination of mRNA and/or degradation of abberant transcripts in a cell, said method comprising: a) providing a cell containing a vector comprising the nucleic acid encoding proteins of the complex, the complex; or an antisense molecule thereof; b) overexpressing said nucleic acid in said cell to produce an overexpressed complex so as to interfere with the function of the complex.

This invention provides method for identifying a disease state involving a defect in the complex comprising: (a) transfecting a cell with a nucleic acid which encodes the complex; (b) determining the proportion of the defective complex of the cell after transfection; (c) comparing the proportion of the defective complex of the cell after transfection with the proportion of defective complex of the cell before transfection.

This invention provides a method for treating a disease associated with peptidyl transferase activity, comprising administering to a subject a therapeutically effective amount of a pharmaceutical composition comprising the complex or the agents, and a pharmaceutical carrier or diluent, thereby treating the subject.

BRIEF DESCRIPTION OF THE DRAWINGS

FIGS. 1A–1B. The yeast Upf1 protein interacts specifically with the peptidyl release factors. (1A) GST-eRF1 or GST-eRF3 fission proteins bind specifically to Upf1p in a yeast extract. Cytoplasmic extracts from a yeast strain BJ3505 transformed with either pG-1 (vector) or pG-1FLAGUPF1 (Flag-Upf1p) were prepared in IBTB and incubated with 30 $\mu$l GST, GST-eRF1 or GST-eRF3 sepharose-protein complexes. The sepharose-protein complexes were washed 2 times in IBTB (see materials and methods), resuspended in SDS-PAGE loading buffer, separated on an 8% SDS-PAGE gel and immunoblotted using anti-FLAG antibody. (1B) Upf1p interacts directly with both eRF1 and eRF3. Upf1p was purified as described previously (Czaplinski et al. 1995). 200 ng of Upf1p was added to 10 $\mu$l of GST, GST-eRF1 or GST-eRF3 sepharose-protein complexes in a total reaction volume of 200 μl in IBTB supplemented with KCl to the final concentration indicated above each lane. After 1 hour at 4° C. sepharose-protein complexes were washed for 3 minutes with 1 ml of IBTB supplemented with KCl to the final concentration indicated above each lane. The purified sepharose-protein complexes were resuspended in SDS-PAGE loading buffer and separated on a 7.5% SDS-PAGE gel and immunoblotted as in (A).

FIGS. 3A–3B. eRF3 and RNA compete for binding to Upf1p. (3A) Poly(U) RNA prevents Upf1p from binding to eRF3. Reaction mixtures were prepared as described in FIG. 1B, except that binding was performed in TBSTB (TBST with 100 μg/ml BSA) and reaction mixtures contained 1 mM ATP, 1 mM GTP, or 100 μg/ml poly(U) RNA as indicated above each lane. The reaction mixtures were mixed for 1 hour at 4° C. Following mixing, the complexes were washed as in FIG. 1B with TBSTB containing 1 mM ATP, 1 mM GTP, or 100 μg/ml poly(U) RNA as indicated above each lane. (3B) Poly(U) RNA does not prevent Upf1 and eRF1 interaction. Reaction mixtures were prepared as in FIG. 1B, in the presence or absence of 100 mg/ml poly(U) RNA as indicated above each lane.

FIGS. (5A–5B). A RENT1/HUPF1 chimeric allele functions in translation termination. (5A) A RENT1/HUPF1 chimeric allele prevents nonsense suppression in a upf1Δ strain. Strain PLY146 (MATΔ ura3-52 trp1Δ upf1::URA3 leu2-2 tyr7-1) was transformed with YCplac22 (vector), YCpUPF1 (UPF1), YCpRent1CHI4-2 or YEpRent1CHI4-2 and cells were grown to OD$_{600}$=0.5 in —trp-met media. Dilutions of 1/10, 1/100 and 1/1000 were prepared in —trp-met media and 5 μl of these dilutions were plated simultaneously on —trp-met (upper plate) or —trp-met-leu-tyr (lower plate) media. Cells were monitored for growth at 30 ° C. (5B) A RENT1/HUPF1 chimeric allele does not promote decay of nonsense containing mRNAs. Total RNA was isolated from cells at OD$_{600}$=0.8 from the strains described in (A). 40 μg RNA from strains PLY146 transformed with YCplac22 (vector), YCpUPF1 (UPF1), or YEpRent1CHI4-2 (YEpRENT1CHI4-2)(10) was subjected to northern blotting analysis and probed with either the LEU2, TYR7 or CYH2 probes.

Figure 6:
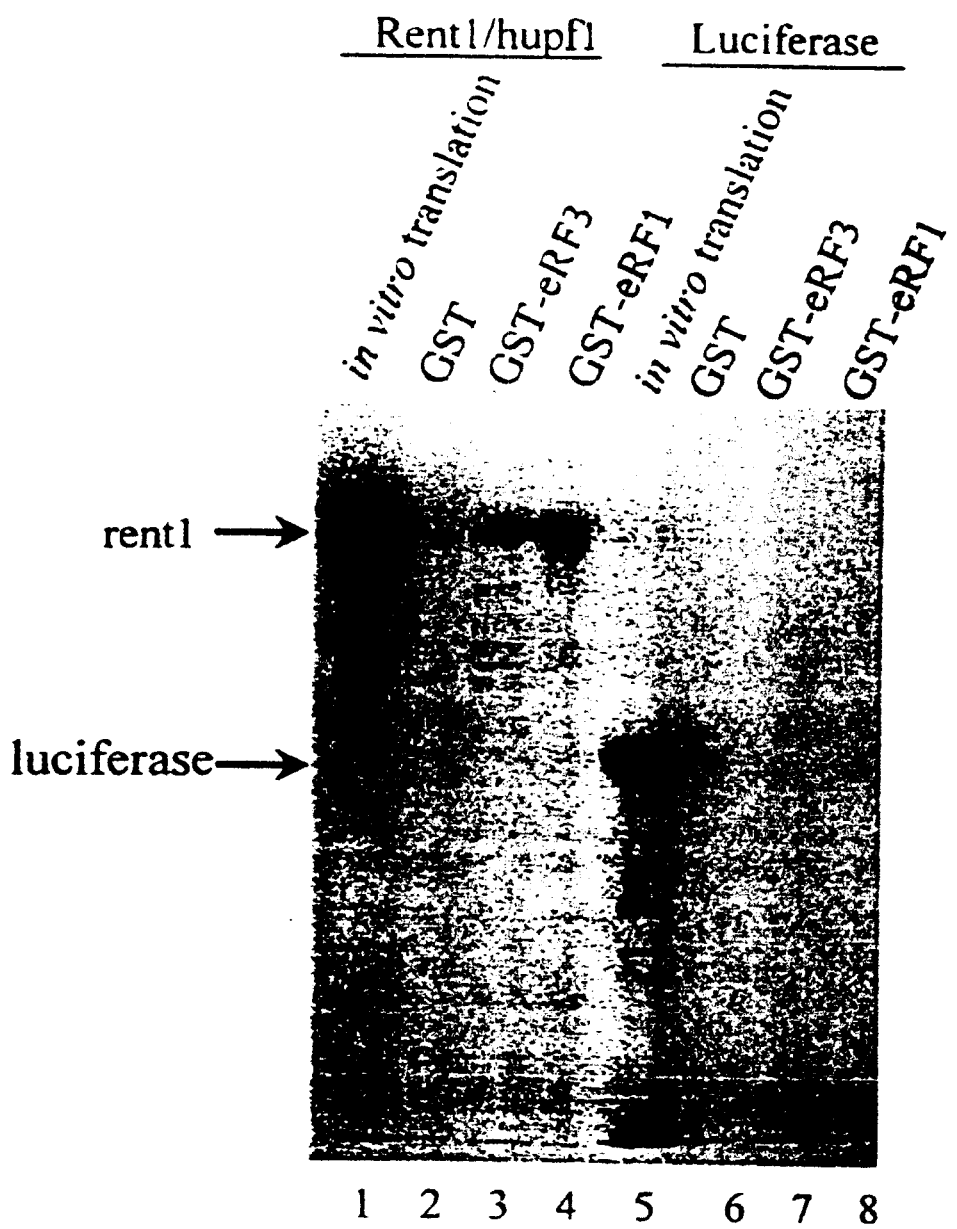

FIG. 6. Rent1/hupf1 interacts with eRF1 and eRF3. NotI linearized pT7RENT1 (lanes 1–4) or luciferase template (lanes 5–8) was used in the TNT coupled Reticulocyte in vitro transcription translation as per manufacturers directions (Promega). 2 μl of completed translation reactions were electrophoresed in lanes 1 and 5. 5 μl of the completed reactions were incubated in 200 μl of IBTB with 10 μl of GST, GST-eRF1 or GST-eRF3 sepharose-protein complexes as indicated above each lane.

Following mixing for 1 hour at 4° C., the sepharose-protein complexes were washed as in FIG. 1A, and the bound proteins were subjected to SDS-PAGE in an 8% gel. Following electrophoresis, gels were fixed for 30 minutes in 50% methanol, 10% acetic acid, and then treated with 1M salicylic acid for 1 hour. Gels were dried and subjected to autoradiography.

FIGS. 7A–7B. Model for Upf1 function in mRNA surveillance. (7A) Modulation of RNA binding enhances interaction of Upf1 with peptidyl release actors. ATP binding to Upf1p decreases the affinity of Upf1 for RNA. Since RNA and eRF3 compete for binding to Upf1, Interaction with eRF3 is favored. (7B) A model for mRNA surveillance. Interaction of Upf1p with peptidyl release factors assembles an mRNA surveillance complex at a termination event. This interaction prevents Upf1 from binding RNA and hydrolyzing ATP, and enhances translation termination. Following peptide hydrolysis, the release factors dissociate from the ribosome, activating the Upf1p helicase activity. The surveillance complex then scans 3' of the termination codon for a DSE. Interaction of the surveillance complex with the DSE signals that premature translation termination has occurred and the mRNA is then decapped and degraded by the Dcp1p and Xrn1p exoribonuclease, respectively.

Figure 8:
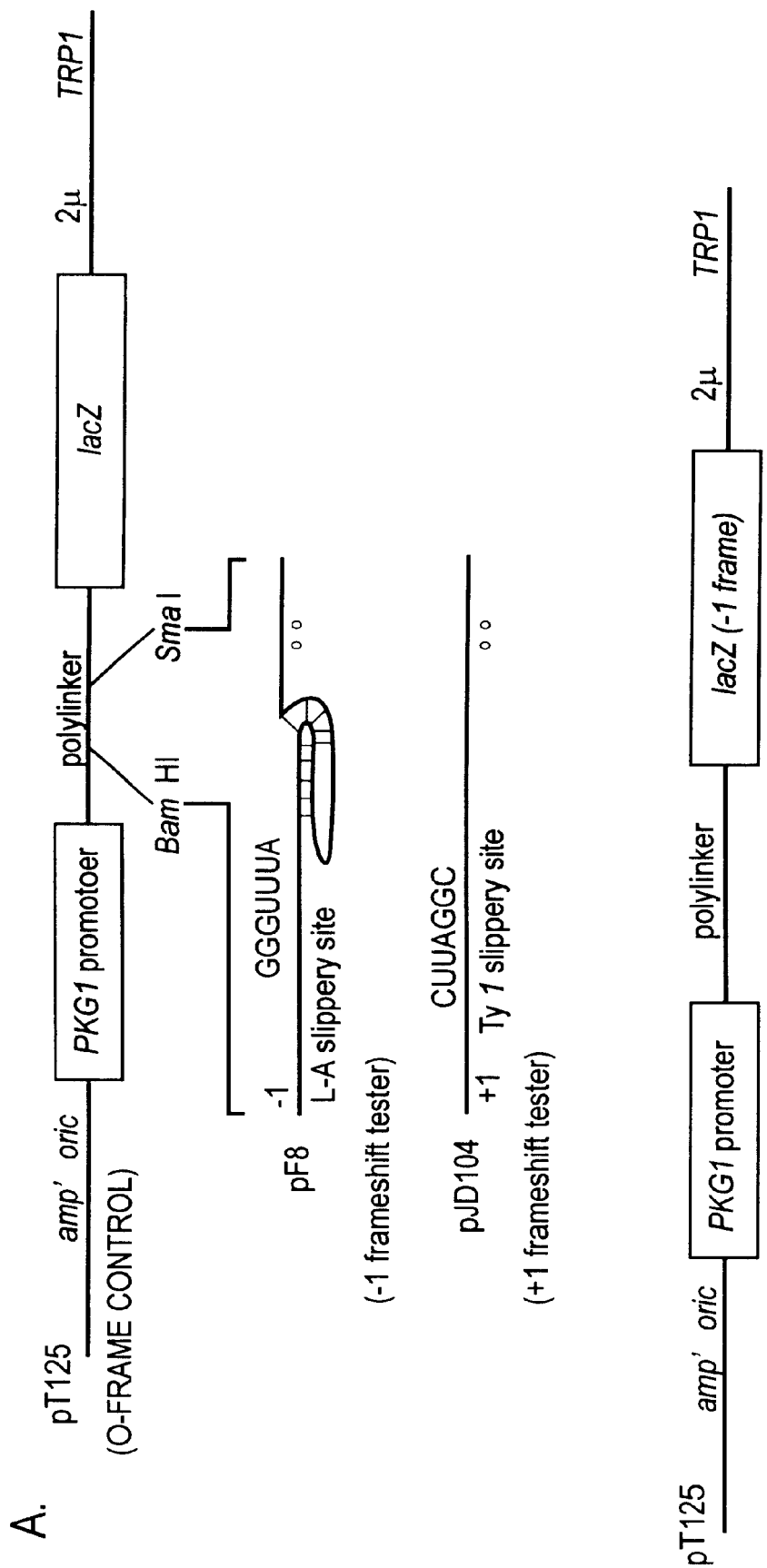

FIG. 8. Schematic diagram of the vectors used to measure programmed −1 ribosomal frameshift efficiencies in vivo. Transcription is driven from the PGK1 promoter and uses the PGK1 translation initiation codon. In pTI25, the bacterial lacZ gene is in the 0-frame with respect to the start site. In plasmid pF8, the lacZ gene is positioned 3' of the L-A virus frameshift signal and in the −1 frame relative to the translation start site.

Figure 9:
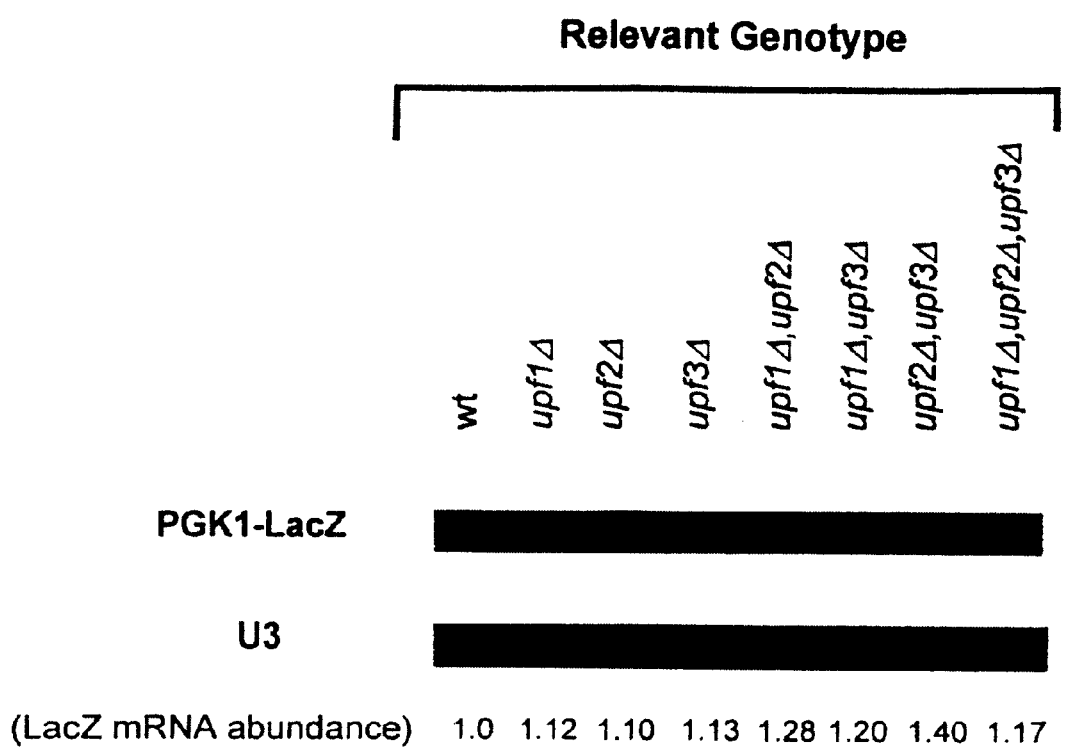

FIG. 9. A upf3Δ strain increases programmed −1 ribosomal frameshifting independently of its ability to promote stabilization of nonsense-containing transcripts. The abundance of the PGK1-LacZ −1 reporter mRNA in the different upf deletion strains was determined by RNase protection analysis. The abundance of the U3 snRNA was used as an internal control for loading. The abundance of the reporter transcript in the wild-type strain was taken arbitrarily as 1.0.

Figure 10:
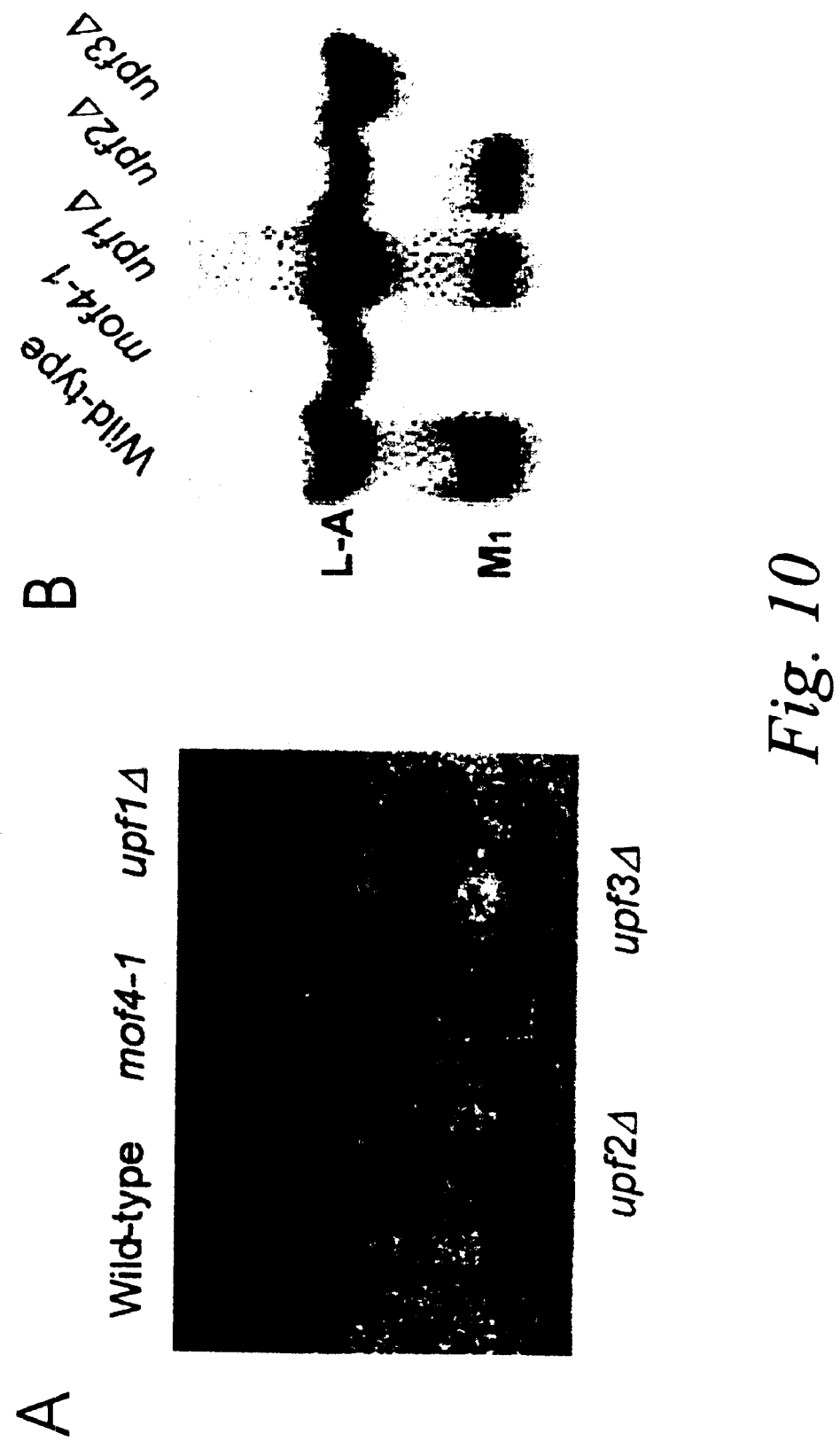

FIG. 10. A upf3Δ strain can not mantain the $M_1$ killer virus. A. Killer assay of upf mutant strains. Colonies of these strains were grown onto a lawn of cells which are sensitive to the secreted killer toxin produced by the $M_1$ virus. Killer activity was observed as a zone of growth inhibition around the colonies. B. Total RNAs were isolated from the same strains and analyzed by Northern Blotting for the presence of L-A and $M_1$ viral RNAs.

FIG. 11. Paromomycin sensitivity was monitored in isogenic wild-type and upf3Δ strains by placing a disc containing 1 mg of paromomycin onto a lawn of cells and determining the zone of growth inhibition around the disc.

DETAILED DESCRIPTION OF THE INVENTION

Transcripts with premature nonsense codons are rapidly degraded thus preventing synthesis of incomplete and potential deleterious proteins. The surveillance pathway eliminates aberrant mRNA that contains non-sense mutations with the protein coding region. This invention is directed to three aspects of post-transcriptional regulation, including:

suppression of nonsense mutations in inherited disease and cancers; inhibition of ribosomal frameshifting in viral infections; and alterations of RNA: protein interactions that, in turn, will modulate critical mRNA levels in multiple diseases.

The Upf1p enhances translation termination by interacting with the peptidyl release factors eucaryotic Release Factor 1 (eRF1) and Release Factor 3 (eRF3) to augment their activity. Both eRF1 and eRF3 are conserved proteins that interact and promote peptidyl release in eucaryotic cells. In yeast, eRF1 and eRF3 are encoded by the SUP45 and SUP35 genes, respectively (Frolova et al. 1994, Zhouravleva et al. 1995). Sup45p and Sup35p have been shown to interact (Stansfield et al 1995, Paushkin et al 1997). eRF1 contains intrinsic peptide hydrolysis activity while eRF3, which has homology to the translation elongation factor EF1α (Didichenko et al. 1991), demonstrates GTPase activity (Frolova et al. 1996), and enhances the termination activity of eRF1 (Zhouravleva et al. 1995). The results presented herein demonstrate a biochemical interaction between the human and yeast Upf1p and the peptidyl release factors eRF1 and eRF3.

The following is a model for how the NMD pathway functions to enhance translation termination and subsequently recognize and degrade a nonsense-containing transcript. A termination codon in the A site of a translating ribosome causes the ribosome to pause (Step 1). The translation termination factors eRF1 and eRF3 interact at the A site and promote assembly of the surveillance complex by interacting with Upf1p, which is most likely complexed with other factors (Step 2). The interaction of Upf1p with the release factors inhibits its ATPase and RNA binding activities. This inhibition may be necessary in order for the Upf1p to enhance the activity of the termination factors and ensure that the Upfp complex does not prematurely disassociate from release factors and search for a DSE. Peptide hydrolysis occurs while the release factors are associated with the surveillance complex. Following GTP hydrolysis by eRF3 and completion of termination, the eRFs disassociate from the ribosome (Step 3). Disassociation of the release factors activates the RNA binding and ATPase activities of the Upf1p and triggers the Upfp complex to scan 3' of the termination codon in search of a DSE (Step 4). If the complex becomes associated with the DSE or DSE-associated factors, an RNP complex forms such that the RNA is a substrate for rapid decapping by Dcp1p (Step 5). The RNP complex that forms as a consequence of the surveillance complex interacting with the DSE prevents the normal interaction between the 3' poly(A)-PABP complex and the 5' cap structure. The uncapped mRNA is subsequently degraded by the Xrn1p exoribonuclease (Step 6).

As defined herein a "surveillance complex" comprises at least Upf1p; and eucaryotic Releasing Factor 1 and 3. The "UPF1" gene, is also called RENT1 or HUPF1. The complex may also comprise Upf2p and /or Upf3p.

A large number of observations point to an important role for protein synthesis in the mRNA decay process. In fact, it appears that these two processes have co-evolved and that factors essential for one process also function in the other. Evidence for this linkage includes experiments demonstrating that: a) drugs or mutations that interfere with translational elongation promote mRNA stabilization, b) sequence elements that dictate rapid mRNA decay can be localized to mRNA coding regions and the activity of such elements depends on their translation, c) degradative factors can be ribosome-associated, and d) premature translational termination can enhance mRNA decay rates Since the quantity of a particular protein synthesized in a given time depends on the cellular concentration of its mRNA it follows that the regulation of mRNA decay rates provides a powerful means of controlling gene expression. In mammalian cells, mRNA decay rates (expressed as half-lives) can be as short as 15–30 minutes or as long as 500 hours. Obviously, such differences in mRNA decay rates can lead to as much as 1000-fold differences in the level of specific proteins. An additional level of control is provided by the observation that decay rates for individual mRNAs need not be fixed, but can be regulated as a consequence of autogenous feedback mechanisms, the presence of specific hormones, a particular stage of differentiation or the cell-cycle, or viral infection.

Perhaps the best examples of the integration of translation and mRNA decay are studies documenting the consequences of premature translational termination. This occurs when deletion, base substitution, or frameshift mutations in DNA lead to the synthesis of an mRNA that contains an inappropriate stop codon (nonsense codon) within its protein coding region. The occurrence of such a premature stop codon arrests translation at the site of early termination and causes the synthesis of a truncated protein. Regardless of their "normal" decay rates, mRNAs transcribed from genes that harbor nonsense mutations (dubbed "nonsense-containing mRNAs") are degraded very rapidly. Such "nonsense-mediated mRNA decay" is ubiquitous, i.e., it has been observed in all organisms tested, and leads to as much as ten-to one hundred-fold reduction in the abundance of specific mRNAs. The combination of severely reduced mRNA abundance and prematurely terminated translation causes reductions in the overall level of expression of specific genes that are as drastic as the consequences of gene deletion. The importance of nonsense-mediated mRNA decay to human health is illustrated by the identification of a growing number of inherited disease in which nonsense mutations cause the disease state and in which nonsense mutations cause the disease state and in which the respective mRNAs have been shown to be substrates of the nonsense-mediated mRNA decay pathway.

An important point, is that inactivation of the nonsense-mediated mRNA decay pathway can be accomplished without impeding cellular growth and leads to the restoration of normal levels and normal decay rates for nonsense-containing mRNA's. More significantly, the yeast experiments (and others) demonstrate that, although an mRNA may still contain a nonsense codon, inactivation of this decay pathway allows enough functional protein to be synthesized that cells can overcome the original genetic defect. Thus, it is possible to treat diseases causes by nonsense mutations by downregulating the nonsense-mediated mRNA decay pathway.

This invention provides an isolated, complex comprising a human Upf1p protein, a peptidyl eucaryotic release factor 1 (eRF1) and a peptidyl eucaryotic release factor 3 (eRF3), wherein the complex is effective to modulate peptidyl transferase activity.

Upf1p interacts with the peptidyl release factors eRF1 and eRF3: Upf1p modulates translation termination by interacting with the peptidyl release factors eRF1 and eRF3. eRF1 and eRF3 were individually expressed in *E. coli* as glutathione-S-transferase (GST) fusion proteins and purified using glutathione sepharose beads. The purified GST-RF (release factor) fusion proteins associated with the glutathione sepharose beads were added to a yeast cytoplasmic extract containing a FLAG epitope-tagged Upf1p. Following incubation, the GST-RFs and associated proteins were purified by affinity chromatography and. subjected to SDS-PAGE. Immunoblotting was performed and the presence of the Upf1p was assayed using an antibody against the FLAG epitope. The anti-FLAG antibody recognized only the 109 kD Upf1p in cytoplasmic extracts from cells transformed with plasmid expressing the FLAG-Upf1p. This analysis also demonstrated that the Upf1p specifically co-purified with either eRF1 or eRF3. Upf1p did not co-purify with GST protein that was not fused to another protein or a GST-JIP protein, in which a Jak2 interacting protein fused to GST was used to monitor the specificity of the reaction.

The interaction of purified Upf1p with either eRF1 or eRF3 was also monitored. The purification for epitope tagged Upf1p (FLAG-Upf1p) has been described previously. Purified FLAG-Upf1p was incubated with the GST-RF fusion proteins in the presence of increasing salt concentrations and the interactions of these proteins were monitored as described above. The results demonstrated that the purified FLAG-Upf1p interacted with either eRF1 or eRF3. The Upf1p-eRF3 complex was less sensitive to increasing salt concentrations than the Upf1-eRF1 complex. The interactions were specific, since the purified Upf1p did not interact with the GST protein or GST-JIP. Interaction of Upf1p with either eRF1 or eRF3 was shown to be dose-dependent.

In one embodiment, the complex further comprises human Upf3p. The results presented here indicate that the Upf3p has a function in ensuring appropriate maintenance of translational reading frame. The function of the Upf3p in this process appears to be genetically epistatic to the Upf1p and Upf2p, since the programmed −1 frameshifting and killer maintenance phenotypes of a upf3Δ are observed in upf1Δ and upf2Δ strains. The results presented here demonstrate that the Upfp's have distinct roles that can affect different aspects of the translation and mRNA turnover processes. Importantly these results may also have practical implications, since many viruses of clinical, veterinary and agricultural importance utilize programmed frameshifting. Thus, programmed ribosomal frameshifting serves as a unique target for antiviral agents, and the identification and characterization of the factors involved in this process will help to develop assays to identify these compounds. In another embodiment, the complex comprises human Upf2p.

This invention provides an expression vector which comprises a nucleic acid encoding a human Upf1p protein, a peptidyl eucaryotic release factor 1 (eRF1) and a peptidyl eucaryotic release factor 3 (eRF3) operably linked to a regulatory element.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [*IRL Press, (1986)*]; B. Perbal, *A Practical Guide To Molecular Cloning* (1984); F. M. Ausubel et al. (eds.), *Current Protocols in Molecular Biology*, John Wiley & Sons, Inc. (1994).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for-transcription and translation.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

Transcriptional and translational control sequences are DNA regulatory sequences, such as promoters, enhancers, terminators, and the like, that provide for the expression of a coding sequence in a host cell. In eukaryotic cells, poly-adenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. A coding sequence is "under the control" of transcriptional and translational control sequences in a cell when RNA polymerase transcribes the coding sequence into mRNA, which is then trans-RNA spliced and translated into the protein encoded by the coding sequence.

A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2 μ plasmid.

Expression of DNA which encodes the proteins, Upf1p, Upf2p, Upf3p, and Release Factor 1 and 2 of the complex, i.e. may be controlled by any promoter/enhancer element known in the art, but these regulatory elements must be functional in the host selected for expression. Promoters which may be used are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 981, Proc. Natl. Acad. Sci. U.S.A. 78:1441–1445), the regulatory sequences of the metallothionein gene (Brinster et al., 1982, Nature 296:3942); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25).

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

This invention provides an agent which binds to the complex comprising an amount of a human Upf1p protein, a peptidyl eucaryotic release factor 1 (eRF1) and a peptidyl eucaryotic release factor 3 (eRF3) effective to modulate translation termination. This invention provides an agent which binds to the complex, wherein the agent inhibits ATPase of Upf1p; GTPase activity of eRF1 or eRF3; RNA binding; binding of the factors to the ribosome; or binding of the factors to each other. This invention provides an agent which inhibits or modulates the binding of human Upf1p to eRF1, or eRF3 or eRF1 or eRF3 to Upf1p; RNA binding; or binding of the factors to the ribosome; binding of the factors to each other. This invention provides an agent which inhibits or modulates the binding of human Upf3 p to eRF1, or eRF3, or eRF1 or eRF3 to Upf3p. This invention provides an agent which facilitates the binding of human Upf1p to eRF1 or eRF3; or eRF3 or eRF1 or eRF3 to Upf1p. This invention provides an agent which facilitates the binding of human Upf3p to eRF1 or eRF3; or eRF3 or eRF1 or eRF3 to Upf3p; RNA binding; or binding of the factors to the ribosome; binding of the factors to each other. This invention provides an agent which modulates the binding of human Upf1p, eRF1 or eRF3 to a ribosome.

This invention provides an antibody which binds to the complex. The antibody may be a monoclonal or polyclonal antibody. Further, the antibody may be labeled With a detectable marker that is either a radioactive, calorimetric, fluorescent, or a luminescent marker. The labeled antibody may be a polyclonal or monoclonal antibody. In one embodiment, the labeled antibody is a purified labeled antibody. Methods of labeling antibodies are well known in the art.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. Such antibodies include but are not limited to polyclonal, monoclonal, chimeric, single chain, Fab fragments, and an Fab expression library. Further the protein or antibody may include a detectable marker, wherein the marker is a radioactive, colorimetric, fluorescent, or a luminescent marker.

Antibodies can be labeled for detection in vitro. e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The protein can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Complex specific antibodies and nucleic acids can be used as probes in methods to detect the presence of a complex polypeptide (using an antibody) or nucleic acid (using a nucleic acid probe) in a sample or specific cell type. In these methods, a complex-specific antibody or nucleic acid probe is contacted with a sample from a patient suspected of having a complex associated disorder, and specific binding of the antibody or nucleic acid probe to the sample detected. The level of the complex or nucleic acid present in the suspect sample can be compared with the level in a control sample, e.g., an equivalent sample from an unaffected individual to determine whether the patient has a complex-associated disorder. Complex polypeptides, or fragments thereof, can also be used as probes in diagnostic methods, for example, to detect the presence of complex-specific antibodies in samples. Additionally, complex-specific antibodies could be used to detect novel cofactors which have formed a complex with the complex or fragment thereof.

This invention provides a method of modulating peptidyl transferase activity during translation, comprising contacting a cell with the complex in an amount effective to facilitate translation termination, thereby modulating the peptidyl transferase activity.

This invention provides a method of modulating peptidyl transferase activity during translation, comprising contacting a cell with the agent, in an amount effective to suppress non-sense translation termination, thereby modulating the peptidyl transferase activity. The peptidyl transferase activity during translation occurs during initiation, elongation, termination and degradation of mRNA.

This invention provides a method of modulating the efficiency of translation termination of mRNA at a non-sense codon and/or promoting degradation of aberrant transcripts, comprising contacting a cell with the agent, in an amount effective to inhibit the binding of human Upf1p to eRF1, or eRF3; or eRF1 or eRF3 to Upf1, thereby modulating the efficiency of translation termination of mRNA at a non-sense codon and/or promoting degradation of aberrant transcripts.

This invention provides a method of modulating the efficiency of translation termination of mRNA at a non-sense codon and/or promoting degradation of aberrant transcripts, comprising contacting a cell with an agent, which inhibits the ATPase/helicase activity of Upfp1; the GTPase activity of eRF1 or eRF3; RNA binding; or binding of RNA to a ribosome, thereby modulating the efficiency of translation termination of mRNA at a non-sense codon and/or promoting degradation of aberrant transcripts.

In a specific embodiment. agents that interfere with NTPase activity, such as, ATPase activity, GTPase, helicase activity, or zinc finger motif configuration may be selected for testing. Such agents may be useful drugs for treating viral infections, since many retroviruses, notably HIV, coronaviruses, and other RNA viruses that are associated with medical and veterinary pathologies. By providing the identity of proteins that modulate frameshifting events, an initial screen for agents may include a binding assay to such proteins. This assay may be employed for testing the effectiveness of agents on the activity of frameshift associated proteins from human as well as yeast or other non-human source, including but not limited to animals.

For example, identification of agents that inhibit the decay pathway, stabilize nonsense transcripts or modulate the efficiency of translation termination are important for the success of antisense RNA technology. Antisense RNAs are small, diffusible, untranslated and highly structured transcripts that pair to specific target RNAs at regions of complementarity, thereby controlling target RNA function or expression. However, attempts to apply antisense RNA technology have met with limited success. The limiting factor appears to be in achieving sufficient concentrations of the antisense RNA in a cell to inhibit or reduce the expression of the target gene. It is likely that one impediment to achieving sufficient concentration is the nonsense decay pathway, since the short antisense RNA transcripts, which are not meant to encode a gene product, will likely lead to rapid translation termination if translation occurs, and consequently to rapid degradation and low abundance of the antisense RNA in the cell. Thus, the agents of the invention that stabilize aberrant mRNA transcripts may also stabilize antisense RNAs.

Presence, relative abundance, or absence of the complex is determined by the binding of the antibody. Possible detection methods including affinity chromatography, Western blotting, or other techniques well known to those of ordinary skill in the art.

This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (see Marcus-Sekura, 1988, Anal. Biochem. 172:298). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro (Marcus-Sekura, 1988, supra; Hambor et al., 1988, J. Exp. Med. 168:1237).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in and RNA molecule and cleave it (Cech, 1988, J. Am. Med. Assoc. 260:3030). Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

This invention provides a method of screening for a drug involved in peptidyl transferase activity during translation comprising: a) contacting cells with a candidate drug; and b) assaying for modulation of the complex, wherein a drug that modulates complex is involved in peptidyl transferase activity. Further, the complex may be assayed for NTPase activity, such as ATPase, GTPase, RNA binding acitivty, factors which bind to the complex, such as but not limited to eRF1 and eRF3, factors which dissociate from the ribosome, factors which promote aggregation; factors which enhance translation termination by slowing peptide hydrolysis.

This invention provides a method of screening for a drug active involved in enhancing translation termination comprising: a) contacting cells with a candidate drug; and b) assaying for modulation of the protein complex; wherein a drug that modulates protein complex is involved in enhancing translation termination.

This invention provides a method of screening for a drug involved in enhancing translation termination comprising: a) incubating the drug and the complex; and b) measuring the effect on non-sense suppression, thereby screening for a drug involved in enhancing translation termination. The assays may be a RNA or NTPase assays, such as ATPase, or GTPase assays which are known to those skilled in the art.

For example, the presence, relative abundance of, or absence of the complex may be detected by binding to an antibody. Upf1 may be detected using the M2 mouse monoclonal antibody against the FLAG epitope as described previously (Czaplinski et al. 1995, Weng et al. 1996a,b). eRF3 was detected as described in Didichenko et al. 1991. eRF1 was detected as described in Stansfield et al. 1992. Upf1p RNA-dependent ATPase activity may be determined using 20 ng Upf1p in the presence of GST-RF fusion proteins by a charcoal assay as described previously (Czaplinski et al. 1995) using 1 µg/ml poly(U) RNA with and 100 µg/ml BSA. The results are plotted as pmol of $^{32}P$ released versus the concentration of the indicated protein. RNA binding may be determined as follows: A uniformly labeled 32 nt RNA was synthesized by SP6 transcription of SstI digested pGEM5Zf(+) as described previously (Czaplinski et al. 1995). RNA binding buffer was as described previously (Czaplinski et al. 1995) with the exception that 100 µg/ml BSA was included in all reactions. The indicated amounts of GST-eRF3 (28), were incubated with 200 ng Upf1p for 15 minutes at 4° C. 50 fmol of the RNA substrate was added and incubated for 5 minutes. Stop solution was added, and reactions electrophoresed in a 4.5% native PAGE gel (0.5×TBE, 30:0.5 acrylamide:bisacrylamide, with 5% glycerol).

This invention provides a method of modulating the efficiency of translation termination of mRNA and/or degradation of aberrant transcripts in a cell, said method comprising: a) providing a cell containing a vector comprising the nucleic acid encoding the complex; or an antisense thereof; b) overexpressing said nucleic acid vector in said cell to produce an overexpressed complex so as to interfere or inhibit with the function of the complex.

This invention provides method for identifying a disease state involving a defect in the complex of claim 1 comprising: (a) transfecting a cell with a nucleic acid which encodes the complex; (b) determining the proportion of the defective complex of the cell after transfection; (c) comparing the proportion of the defective complex of the cell after transfection with the proportion of defective complex of the cell before transfection.

As noted above, nonsense-mediated mRNA decay leads to cellular deficiencies of essential proteins and hence to disease. Altered control of the stability of normal mRNAs can have comparably dire consequences.

This invention provides a method for treating a disease associated with peptidyl transferase activity, comprising administering to a subject a therapeutically effective amount of a pharmaceutical composition comprising the complex of claim 1 or the agents which modulate or stimulate the complex, and a pharmaceutical carrier or diluent, thereby treating the subject.

Nonsense mutations cause approximately 20–40% of the individual causes of over 2 different inherited diseases (including cystic fibrosis, hemophilia, familial hypercholesterolemia, retinitis pigmentosa, Duchenne muscular dystrophy, and Marfan syndrome). For many diseases in which only one percent of the functional protein is produced, patients suffer serious disease symptoms, whereas boosting expression to only five percent of normal levels can greatly reduce the severity or eliminate the disease. In addition, a remarkably large number of the most common forms of colon, breast, esophageal, lung, head and neck, bladder cancers result from frameshifting and nonsense mutations in regulatory genes (i.e., p53, BRCA1, BRCA2, etc.). Correcting nonsense mutations in the regulatory genes to permit synthesis of the respective proteins should cause death of the cancer cells.

The disease, proteins, or genes which are as a result of non-sense or frameshift mutations include but are not limited to the following: HEMOGLOBIN—BETA LOCUS; CYSTIC FIBROSIS TRANSMEMBRANE CONDUCTANCE REGULATOR; MUSCULAR DYSTROPHY, PSEUDOHYPERTROPHIC PROGRESSIVE, DUCHENNE AND BECKER,TYPES; PHENYLKETONURIA, INSULIN RECEPTOR; HEMOPHILIA A, ADENOMATOUS POLYPOSIS OF THE COLON, HYPERCHOLESTEROLEMIA, FAMILIAL, NEUROFIBROMATOSIS, TYPE I, HEMOPHILIA B, HYPERLIPOPROTEINEMIA TYPE I, TAY-SACHS DISEASE, BREAST CANCER TYPE 1, ADRENAL HYPERPLASIA, VON WILLEBRAND DISEASE, MUCOPOLYSACCHARIDOSIS TYPE I, ALBINISM I, POLYCYSTIC KIDNEY DISEASE 1, ORNITHINE AMINOTRANSFERASE DEFICIENCY ANGIOKERATOMA. DIFFUSE MULTIPLE ENDOCRINE NEOPLASIA TYPE 1, SEX-DETERMINING REGION Y, SOLUTE CARRIER FAMILY 4 ANION EXCHANGER MEMBER 1, COLLAGEN TYPE I ALPHA-1 CHAIN, HYPOXANTHINE GUANINE PHOSPHORIBOSYLTRANSFERASE 1, GLUCOKINASE, TUMOR PROTEIN p53, PROTEOLIPID PROTEIN, MYELIN, GROWTH HORMONE RECEPTOR, LUTEINIZING HORMONE/CHORIOGONADOTROPIN RECEPTOR;, APOLIPOPROTEIN A-I OF HIGH DENSITY LIPOPROTEIN, GLUCOSE-6-PHOSPHATE DEHYDROGENASE, ORNITHINE TRANSCARBAMYLASE DEFICIENCY HYPERAMMONEMIA, XERODERMA PIGMENTOSUM I, PAIRED BOX HOMEOTIC GENE 6, VON HIPPEL-LINDAU SYNDROME, CYCLIN-DEPENDENT KINASE INHIBITOR 2A, TUBEROUS SCLEROSIS 2, TYROSINEMIA, TYPE I NORRIE DISEASE, PHOSPHODIESTERASE 6B, PALMITOYL-PROTEIN THIOESTERASE, APOLIPOPROTEIN B. BRUTON AGAMMAGLOBULINEMIA TYROSINE KINASE, ADRENAL HYPOPLASIA, SOLUTE CARRIER FAMILY 5, 5,10-@METHYLENETETRAHYDROFOLATE REDUCTASE, WILMS TUMOR, POLYCYSTIC KIDNEYS, TRANSCRIPTION FACTOR 14, HEPATIC NUCLEAR FACTOR, MUCOPOLYSACCHARIDOSIS TYPE II, PROTEIN C DEFICIENCY, CONGENITAL THROMBOTIC DISEASE DUE TO NEUROFIBROMATOSIS TYPE II, ADRENOLEUKODYSTROPHY, COLLAGEN TYPE VII ALPHA-1, COLLAGEN, TYPE X ALPHA 1, HEMQGLOBIN—ALPHA LOCUS-2, GLYCOGEN STORAGE DISEASE VII, FRUCTOSE INTOLERANCE, BREAST CANCER 2 EARLY-ONSET; BRCA2, FUCOSYLTRANSFERASE 2, HERMANSKY-PUDLAK SYNDROME, THYROGLOBULIN, RETINOBLASTOMA, WISKOTT-ALDRICH SYNDROME, RHODOPSIN, COLLAGEN TYPE XVII, CHOLINERGIC RECEPTOR, CYCLIC NUCLEOTIDE GATED CHANNEL, PHOTORECEPTOR, cGMP GATED, CHOLINERGIC RECEPTOR NICOTINIC EPSILON POLYPEPTIDE, RECOMBINATION ACTIVATING GENE-1, CAMPOMELIC DYSPLASIA, IMMUNODEFICIENCY WITH INCREASED IgM, RET PROTOONCOGENE; RET MUCOPOLYSACCHARIDOSIS TYPE IVA, LEPTIN RECEPTOR, SPHEROCYTOSIS, HEREDITARY, ARGININE VASOPRESSIN, APOLIPOPROTEIN C-II DEFICIENCY TYPE I HYPERLIPOPROTEINEMIA DUE TO CYSTIC FIBROSIS, WILSON DISEASE, LEPTIN, ANGIONEUROTIC EDEMA, CHLORIDE CHANNEL 5, GONADAL DYSGENESIS, PORPHYRIA, ACUTE INTERMITTENT. HEMOGLOBIN, GAMMA A, KRABBE DISEASE, GLYCOGEN STORAGE DISEASE V, METACHROMATIC LEUKODYSTROPHY, LATE-INFANTILE, GIANT PLATELET SYNDROME, VITAMIN D RECEPTOR, SARCOGLYCAN, DELTA, TWIST, DROSOPHILA, ALZHEIMER DISEASE, OSTEOPETROSIS WITH RENAL TUBULAR ACIDOSIS, AMELOGENESIS IMPERFECTA-1, HYPOPLASTIC TYPE, POU DOMAIN, CLASS 1, TRANSCRIPTION FACTOR 1, DIABETES MELLITUS, AUTOS OMAL DOMINANT V-KIT HARDY-ZUCKERMAN 4 FELINE SARCOMA VIRAL ONCOGENE HOMOLOG, HEMOGLOBIN--DELTA LOCUS, ADENINE PHOSPHORIBOSYLTRANSFERASE, PHOSPHATASE AND TENSIN HOMOLOG, GROWTH HORMONE 1, CATHEPSIN K, WERNER SYNDROME. NIEMANN-PICK DISEASE. GROWTH HORMONE-RELEASING HORMONE RECEPTOR, CERULOPLASMIN, COLONY STIMULATING FACTOR 3 RECEPTOR, GRANULOCYTE, PERIPHERAL MYELIN PROTEIN 22, FUCOSIDOSIS, EXOSTOSES MULTIPLE TYPE II, FANCONI ANEMIA, COMPLEMENTATION GROUP C, ATAXIA-TELANGIECTASIA, CADHERIN 1, SOLUTE CARRIER FAMILY 2, MEMBER 2, UDP GLUCURONOSYLTRANSFERASE 1 FAMILY, Al, TUBEROUS SCLEROSIS 1, LAMININ, GAMMA 2, CYSTATIN B, POLYCYSTIC KIDNEY DISEASE 2, MICROSOMAL TRIGLYCERIDE TRANSFER PROTEIN, 88 KD, DIASTROPHIC DYSPLASIA, FLAVIN-CONTAINING MONOOXYGENASE 3, GLYCOGEN STORAGE DISEASE III, POU DOMAIN, CLASS 3, TRANSCRIPTION FACTOR 4, CYTOCHROME P450, SUBFAMILY IID, PORPHYRIA, CONGENITAL ERYTHROPOIETIC, ATPase, Cu(2+)-TRANSPORTING, ALPHA POLYPEPTIDE, COLON CANCER, FAMILIAL, NONPOLYPOSIS TYPE 1, PHOSPHORYLASE KINASE, ALPHA 1 SUBUNIT (MUSCLE), ELASTIN, CANAVAN DISEASE EXCISION-REPAIR, COMPLEMENTING DEFECTIVE, IN CHINESE HAMSTER, 5, JANUS KINASE 3, STEROIDOGENIC ACUTE REGULATORY PROTEIN, FUCOSYLTRANSFERASE 6, GLAUCOMA 1, OPEN ANGLE, EXOSTOSES, MULTIPLE, TYPE I, MYOCILIN, AGRANULOCYTOSIS, INFANTILE GENETIC ERYTHROPOIETIN RECEPTOR, SURVIVAL OF MOTOR NEURON 1, TELOMERIC, SONIC HEDGEHOG, DROSOPHILA, HOMOLOG OF, LECITHIN:CHOLESTEROL ACYLTRANSFERASE DEFICIENCY, POSTMEIOTIC SEGREGATION INCREASED (S. CEREVISIAE)-1, EXCISION-REPAIR CROSS-COMPLEMENTING RODENT REPAIR DEFICIENCY, GROUP 6, MAPLE SYRUP URINE DISEASE APOPTOSIS ANTIGEN 1, TRANSCRIPTION FACTOR 1, HEPATIC, UBIQUITIN-PROTEIN LIGASE E3A, TRANSGLUTAMINASE 1, MYOSIN VIIA, GAP JUNCTION PROTEIN, BETA-1, 32-KD, TRANSCRIPTION FACTOR 2, HEPATIC, PROTEIN 4.2, ERYTHROCYTIC, THYROID-STIMULATING HORMONE, BETA CHAIN, TREACHER COLLINS-FRANCESCHETTI SYNDROME 1, CHOROIDEREMIA, ENDOCARDIAL FIBROELASTOSIS-2, COWDEN DISEASE, ANTIMULLERIAN HORMONE, SRY-BOX 10, PTA DEFICIENCY TYROSINASE-RELATED PROTEIN 1, PHOSPHORYLASE KINASE, BETA SUBUNIT, SERINE/THREONINE PROTEIN KINASE 11, PHOSPHOLIPASE A2, GROUP IIA, EXCISION-REPAIR, COMPLEMENTING DEFECTIVE, IN CHINESE HAMSTER 3, ADRENAL HYPERPLASIA II COLLAGEN, TYPE IV, ALPHA-4 CHAIN, THROMBASTHENIA OF GLANZMANN AND NAEGELI RETINAL PIGMENT EPITHELIUM-SPECIFIC PROTEIN, 65-KD, HOMEO BOX A13, CALPAIN, LARGE POLYPEPTIDE L3, XANTHINURIA LAMININ, ALPHA 2, CYTOCHROME P450, SUBFAMILY XIX, MUCOPOLYSACCHARIDOSIS TYPE VI, CEROID-LIPOFUSCINOSIS, NEURONAL 3, JUVENILE, CITRULLINEMIA MYOCLONUS EPILEPSY OF UNVERRICHT AND LUNDBORG PHOSPHORYLASE KINASE, TESTIS/LIVER, GAMMA 2, SOLUTE CARRIER FAMILY 3, MEMBER 1, PTERIN-4-ALPHA-CARBINOLAMINE DEHYDRATASE, ALBINISM, OCULAR, TYPE 1, LEPRECHAUNISM EPILEPSY, BENIGN NEONATAL, HIRSCHSPRUNG DISEASE OSTEOPETROSIS, AUTOSOMAL RECESSIVE RAS p21 PROTEIN ACTIVATOR 1, MUCOPOLYSACCHARIDOSIS TYPE VII CHEDIAK-HIGASHI SYNDROME, POTASSIUM CHANNEL, INWARDLY-RECTIFYING, SUBFAMILY J, MEMBER 1, PLAKOPHILIN 1, PLATELET-ACTIVATING FACTOR ACETYLHYDROLASE ISOFORM 1B, ALPHA SUBUNIT, PLECTIN 1, SHORT STATURE, MHC CLASS II TRANSACTIVATOR, HYPOPHOSPHATEMIA, VITAMIN D-RESISTANT RICKETS, RIEG BICOID-RELATED HOMEOBOX TRANSCRIPTION FACTOR 1, MUSCULAR DYSTROPHY, LIMB-GIRDLE, TYPE 2E, RETINITIS PIGMENTOSA-3, MutS, E. COLI, HOMOLOG OF, 3, TYROSINE TRANSAMINASE DEFICIENCY LOWE OCULOCEREBRORENAL SYNDROME, XANTHISM NEPHRONOPHTHISIS, FAMILIAL JUVENILE 1, HETEROTAXY, VISCERAL, X-LINKED MILLER-DIEKER LISSENCEPHALY SYNDROME, PROPERDIN DEFICIENCY, X-LINKED 3-@OXOACID CoA TRANSFERASE, WAARDENBURG-SHAH SYNDROME MUSCULAR DYSTROPHY, LIMB-GIRDLE, TYPE 2, ALPORT SYNDROME, AUTOSOMAL RECESSIVE GLYCOGEN STORAGE DISEASE IV DIABETES MELLITUS, AUTOSOMAL DOMINANT, TYPE II SOLUTE CARRIER FAMILY 2, MEMBER 1, HAND-FOOT-UTERUS SYNDROME CYSTINOSIS, EARLY-ONSET OR INFANTILE NEPHROPATHIC TYPE, CRIGLER-NAJJAR SYNDROME INSULINLIKE GROWTH FACTOR 1, LACTATE DEHYDROGENASE-A, STICKLER SYNDROME, TYPE II, AMAUROSIS CONGENITA OF LEBER I ALPHA-GALACTOSIDASE B, ADRENAL HYPERPLASIA I LI-FRAUMENI SYNDROME, SOLUTE CARRIER FAMILY 12, MEMBER 1, KLEIN-WAARDENBURG SYNDROME PEROXISOME BIOGENESIS FACTOR 7, PAIRED BOX HOMEOTIC GENE 8, RETINOSCHISIS, 5-HYDROXYTRYPTAMINE RECEPTOR 2C, URATE OXIDASE, PEUTZ-JEGHERS SYNDROME MITRAL VALVE PROLAPSE, FAMILIAL, MELANOMA, CUTANEOUS MALIGNANT, 2, FUCOSYLTRANSFERASE 1, PYCNODYSOSTOSIS, MUCOPOLYSACCHARIDOSIS TYPE IIIB P-GLYCOPROTEIN-3, SEVERE COMBINED IMMUNODEFICIENCY, B-CELL-NEGATIVE RETINITIS PIGMENTOSA, RIBOSOMAL PROTEIN S6 KINASE, 90 KD, POLYPEPTIDE 3, SYNDROME SYNDROME, FACTOR DEFICIENCY X-LINKED, AGAINST DECAPENTAPLEGIC, DROSOPHILA, HOMOLOG OF, 4, FACTOR FOR COMPLEMENT, DEHYDROGENASE/DELTA-ISOMERASE, TYPE I CONDUCTIVE, WITH STAPES FIXATION AQP1 1, PROGRESSIVE, PROGRESSIVE FAMILIAL INTRAHEPATIC, TYPE III MONOPHOSPHATE DEAMINASE-1, HOMEO BOX TRANSCRIPTION FACTOR 1.

This invention provides methods to screen drugs which acts as therapeutics that treat diseases caused by nonsense and frameshift mutations. By biochemical and in vitro assays which monitor the activity of ATP binding, ATPase activity, RNA helicase activity, GTP binding, GTPase activity, release factors, or RNA binding to the complex or to each other (i.e. Upf1p to eRF1 and eRF3, or Upf2 to Upf3p); developing assays capable of quantitating the activity of the human gene product in mRNA decay and translational suppression; screening compounds using aforementioned assays. The experiments disclosed herein have shown that antagonizing/agonizing the activity of the complex of factors, proteins of the complex can overcome the otherwise lethal effects of nonsense mutations in essential genes or and have established yeast as a model system for drug development for which human agents or compounds may be obtained.

A "test composition", as used herein, is any composition such as a gene, a nucleic acid sequence, a polypeptide, peptide fragment or composition created through the use of a combinatorial library or other combinatorial process that can be assayed for its ability to function in given capacity or compound which mimics the activity of the complex. Often such a test composition, nucleic acid sequence or polypeptide is, because of its sequence or structure, suspected of being able to function in a given capacity.

A "co-factor" is any composition (e.g., a polypeptide, polypeptide derivative, or peptidomimetic) that is capable of modulating the complex and influencing NMRD or efficiency of translation termination. Included are compositions that naturally induce NMRD or the efficiency of translation termination via the complex; also included are compositions that do not naturally induce NMRD (e.g., artificial compositions and natural compositions that serve other purposes). The term "agonist" as used herein means any composition that is capable of increasing or stimulating the efficiency of translation termination or mRNA degradation by interacting with or binding to the complex or factors, such as eRF1 or eRf3, of the complex which interact with Upf1p of the complex. The term "antagonist" as used herein means any composition that is capable of decreasing or inhibiting the efficiency of translation termination or mRNA degradation by interacting with or binding to the complex or factors, such as eRF1 or eRf3, of the complex which interact with Upf1p of the complex.

The invention also provides a method for determining whether a test agent or composition modulates the complex in a cell. The method can be performed by (i) providing a cell that has the complex; (ii) contacting the cell with a test agent or composition that, in the absence of the test agent or composition, activates the complex in the cell; and (iii) detecting a change in the complex of the cell. In practicing the invention, the cell can be contacted with the test agent or composition either simultaneously or sequentially. An increase in the complex indicates that the test agent or composition is an agonist of the complex while a decrease in the complex indicates that the test agent or composition is an antagonist of the complex. If desired, the above-described method for identifying modulators of the complex can be used to identify compositions, co-factors or other compositions within the complex pathway comprising the complex for use in this aspect of the invention. Any agent or composition can be used as a test agent or composition in practicing the invention; a preferred test agent or compositions include polypeptides and small organic agent or compositions. Although sequence or structural homology can provide a basis for suspecting that a test agent or composition can modulate the complex in a cell, randomly chosen test agent or compositions also are suitable for use in the invention. Art-known methods for randomly generating an agent or compositions (e.g., expression. of polypeptides from nucleic acid libraries) can be used to produce suitable test agent or compositions. Those skilled in the art will recognize alternative techniques can be used in lieu of the particular techniques described herein.

The invention also provides a method for detecting novel co-factors or inhibitors which bind the complex which comprises contacting a sample comprising the complex with test compositions and measuring the change in the complex after application of the test composition. The complex of the instant invention is useful in a screening method for identifying novel test compounds or novel test compositions which affect the complex. Thus, in another embodiment, the invention provides a method for screening test compositions comprising incubating components, which include the test composition, and the complex under conditions sufficient to allow the components to interact, then subsequently measuring the effect the test composition has on the complex in a test cell. The observed effect on the complex and a composition may be either agonistic or antagonistic.

This invention provides a method for identifying a disease state involving defective the protein complex comprising: (a) transfecting a cell with a nucleic acid which encodes the protein complex; (b) determining the proportion of the defective protein complex of the cell after transfection; (c) comparing the proportion of the defective protein complex of the cell after transfection with the proportion of defective protein complex of the cell before transfection.

Any screening technique known in the art can be used to screen for agents that affect translation termination or a mRNA decay protein. The present invention contemplates screens for small molecule ligands.

Knowledge of the primary sequence of a translation termination or mRNA decay protein, and the similarity of that sequence with. proteins of known function, can provide an initial clue as to agents that are likely to affect protein activity. Identification and screening of such agents is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

The screening can be performed with recombinant cells that express the proteins, complexes involved in translation termination or mRNA decay protein, or alternatively, with the purified protein. For example, the ability of labeled protein to bind to a molecule in a combinatorial library can be used as a screening assay, as described in the foregoing references.

This invention provides a method of screening a candidate host cell for the amount of the complex produced by said cell relative to a control cell, said method comprising: a) providing a clonal population of said candidate host cell; b) treating said clonal population of cells such that the intracellular proteins are accessible to an antibody; c) contacting said intracellular proteins with an antibody that specifically binds to the complex; and d) determining the relative amount of the complex produced by said candidate host cell.

This invention provides a method of substantially inhibiting translation termination efficiency of mRNA and/or degradation of aberrant transcripts in a cell, said method comprising: a) providing a cell containing the DNA; b) overexpressing said DNA in said cell to produce an overexpressed polypeptide that binds to Upf1p and interferes with Upf1p function.

This invention provides a method of substantially inhibiting translation termination efficiency of mRNA and/or degradation of aberrant transcripts in a cell in a cell, said method comprising: a) providing a cell; b) expressing antisense transcript of the complex in sufficient amount to bind to the complex.

This invention provides a method of substantially inhibiting translation termination in a cell, said method comprising: mutating the complex comprising Upf1p, Upf2p, Upf3p, eRF1, and eRF3, such that essentially no functional complex is produced in said cell.

This invention provides a method for treating a disease associated with translation termination efficiency of mRNA and/or degradation of aberrant transcripts, comprising administering to a subject administering to a subject a therapeutically effective amount of a pharmaceutical composition comprising the complex which is introduced into a cell of a subject; and a pharmaceutical carrier or diluent, thereby treating the subject.

In one embodiment, the invention provides a method of treating a patient having or at risk of having early stage as a result of genetic deficiency, disease or clinical treatment wherein the condition has an etiology associated with a defective, the method comprising administering to the patient a therapeutically effective amount of a formulation or composition which modulates the expression of the complex such that the state of the patient is ameliorated.

"Therapeutically effective" as used herein, refers to an amount formulation that is of sufficient quantity to ameliorate the state of the patient so treated. "Ameliorate" refers to a lessening of the detrimental effect of the disease state or disorder in the patient receiving the therapy. The subject of the invention is preferably a human, however, it can be envisioned that any animal can be treated in the method of the instant invention. The term "modulate" means enhance, inhibit, alter, or modify the expression of the complex, mRNA, nucleic acid, polypeptide or protein.

This has obvious implications for drug targeting, in that one or the other domain can be targeted for drug developement, e.g., using the combinatorial library techniques or rational drug design techniques.

In view of the foregoing, it becomes apparent that the present invention provides a number of routes for affecting translation termination, which has important implications for antiviral therapy and for suppression of pathological nonsense mutations. Thus, the present invention provides drugs for use as antiviral compounds or to alter ribosomal decay.

The term "drugs" is used herein to refer to a compound or agents, such as an antibiotic or protein, that can affect function of the peptidyl transferase center during initiation, elongation, termination, mRNA degradation. Such compounds can increase or decrease aberrant mRNA and the efficiency of translation termination.

Gene Therapy and Transgenic Vectors

In one embodiment, a nucleic acid encoding the complex or factors of the complex; an antisense or ribozyme specific for the complex, or specific for regions of the release factors and Upf1p, are introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845. Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancrease, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a further embodiment, the present invention provides for co-expression of a gene product that modulates activity at the peptidyl transferase center and a therapeutic heterologous antisense or ribozyme gene under control of the specific DNA recognition sequence by providing a gene therapy expression vector comprising both a gene coding for a modulator of a peptidyl transferase center (including but not limited to a gene for a mutant frameshift or mRNA decay protein, or an antisense RNA or ribozyme specific for mRNA encoding such a protein) with a gene for an unrelated antisense nucleic acid or ribozyme under coordinated expression control. In one embodiment, these elements are provided on separate vectors; alternatively these elements may be provided in a single expression vector.

Antiviral Therapy

In yet a further embodiment, the present invention provides the means to treat viral infections by providing agents that modulate translation termination, and thus directly affect viral replication or assembly of viral particles.

The present invention advantageously provides drugs and methods to identify drugs for use in antiviral (or nonsense suppression) therapy of viruses that use the basic −1 ribosomal frameshifting mechanism, which includes four large families of animal viruses and three large families of plant viruses. Specifically, this invention provides assays for screening agents, antagonist/agonists, which effect frameshifting involving the complex, and which involve Upf3p. Also, this invention provides a mutant Upf3.

For example, almost all retroviruses use −1 ribosomal frameshifting, including lentiviruses (immunodeficiency viruses) such as HIV-1 and HIV-2, SIV, FIV, BIV, Visna virus, Arthritis-encephalitis virus, and equine infectious anemia virus; spumaviruses (the foamy viruses), such as human foamy virus and other mammalian foamy viruses; the T cell lymphotrophic viruses, such as HTLV-I, HTLV-II, STLVs, and BLV; avian leukosis viruses, such as leukemia and sarcoma viruses of many birds, including commercial poultry; type B retroviruses, including mouse mammary tumor virus; and type D retroviruses, such as Mason-Pfizer monkey virus and ovine pulmonary adenocarcinoma virus. In addition, many coronaviruses use the −1 frameshifting, including human coronaviruses, such as 229-E, OC43; animal coronaviruses, such as calf coronavirus, transmissible gastroenteritis virus of swine, hemagglutinating encephalomyelitis virus of swine, and porcine epidemic diarrhea virus; canine coronavirus; feline infectious peritonitis virus and feline enteric coronavirus; infectious bronchitis virus of fowl and turkey bluecomb virus; mouse hepatitis virus, rat coronavirus, and rabbit coronavirus. Similarly, torovirus (a type of coronavirus) is implicated, such as human toroviruses associated with enteric and respiratory diseases; breda virus of calves and bovine respiratory virus; berne virus of horses; porcine torovirus; feline torovirus. Another coronavirus is the arterivirus, which includes simian hemorrhagic fever virus, equine arteritis virus, Lelystad virus (swine), VR2332 virus (swine), and lactate dehydrogenase-elevating virus (rodents). Other animal viruses are paramyxoviruses, such as human −1 ribosomal frameshifting reported in measles, and astroviruses, such as human astroviruses 1–5, and bovine, ovine, porcine, canine, and duck astroviruses.

The plant viruses that involve a −1 frameshifting mechanism include tetraviruses, such as sobemoviruses (e.g., southern bean mosaic virus, cocksfoot mettle virus), leuteoviruses (e.g., barley yellowswarf virus, beet western yellows virus, and potato leaf roll virus), enamoviruses (e.g., pea mosaic virus), and umbraviruses (e.g., carrot mottle virus); tombusviruses, such as tombusvirus (e.g., tomato bushy stunt virus), carmovirus (e.g., carnation mottle virus), necrovirus (e.g., tobacco necrosis virus); dianthoviruses (e.g., red clover necrotic mosaic virus), and machiomovirus (e.g., maize chlorotic mottle virus).

In addition, totiviruses, such as L-A and L-BC (yeast) and other fungal viruses, giradia lamblia virus (intestinal parasite), triconella vaginell virus (human parasite), leishmania brasiliensis virus (human parasite), and other protozoan viruses are −1 frameshift viruses.

According to the invention, the component or components of a therapeutic composition of the invention may be introduced or administered parenterally, paracancerally, transmucosally, transdermally, intramuscularly, intravenously, intradermaly, subcutaneously, intraperitonealy, intraventricularly, or intracranialy.

Modes of delivery include but are not limited to: naked DNA, protein, peptide, or within a viral vector, or within a liposome. In one embodiment the viral vector is a retrovirus, adeno-associated virus, or adenovirus.

As can be readily appreciated by one of ordinary skill in the art, the compositions and methods of the present invention are particularly suited to treatment of any animal, particularly a mammal, more specifically human. But by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

As used herein, "pharmaceutical composition" could mean therapeutically effective amounts of the complex with suitable diluents, preservatives, solubilizers, emulsifiers, adjuvants and/or carriers useful in SCF therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of SCF. The choice of compositions will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors. ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. As is appreciated by those skilled in the art the amount of the compound may vary depending on its specific activity and suitable dosage amounts may range from about 0.1 to 20, preferably about 0.5 to about 10, and more preferably one to several, milligrams of active ingredient per kilogram body weight of individual per day and depend on the route of administration. In one embodiment the amount is in the range of 10 picograms per kg to 20 milligrams per kg. In another embodiment the amount is 10 picograms per kg to 2 milligrams per kg. In another embodiment the amount is 2–80 micrograms per kilogram. In another embodiment the amount is 5–20 micrograms per kg.

The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In yet another embodiment, the therapeutic compound can be delivered in a controlled release system. For example, the complex may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres. Boca Raton, Fla. (1974); *Controlled Drug Bioavailability, Drug Product Design and Performance*, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release. supra, vol. 2, pp. 115–138 (1984)). Preferably, a controlled release device is introduced into a subject in proximity of the site of inappropriate immune activation or a tumor. Other controlled release systems are discussed in the review by Langer (Science 249:1527–1533 (1990)).

As can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

The present invention may be better understood by reference to the following non-limiting Examples, which are provided as exemplary of the invention.

EXPERIMENTAL DETAILS SECTION

EXAMPLE 1

Enhancement of Translation Termination And Degradation of Aberrant mRNAs

The nonsense-mediated mRNA decay pathway is an example of an evolutionarily conserved surveillance pathway that rids the cell of transcripts that contain nonsense mutations. The product of the UPF1 gene is a necessary component of the putative surveillance complex that recognizes and degrades aberrant mRNAs. The results presented here demonstrate that the yeast and human forms of the Upf1p interact with both eucaryotic translation termination factors eRF1 and eRF3. Consistent with Upf1p interacting with the eRFs, the Upf1p is found in the prion-like aggregates that contain eRF1 and eRF3 observed in yeast [PSI$^+$] strains. These results indicate that interaction of the Upf1p with the peptidyl release factors is a key event in the assembly of the putative surveillance complex that enhances translation termination monitors whether termination has occurred prematurely and promotes degradation aberrant transcripts.

MATERIALS AND METHODS

General yeast methods: Yeast Media was prepared as described (Rose et al. 1990). Yeast Transformations were performed by the lithium acetate method (Scheistl and Geitz 1989). RNA isolation, blotting and hybridization was as described (Weng et al. 1996a, Hagan et al. 1995).

Plasmids: Plasmid YCp and YEp RENTCHI4-2 were created by ligating a 4.5 kb SstI-Asp718 fragment from pMET25CHIMERA (Perlick et al. 1996) harboring the chimeric gene under the MET25 promoter into YCplac22 and YEplac112 (Ferguson et al. 1981) respectively. YCp-FLAGUPF1 and YEpFLAGUPF1 were described previously (Weng et al. 1996a). GST-RF fusion plasmids pGEX2T, pGEX2T-SUP35 and pGEX2T-SUP45 were described previously (Paushkin et al. 1997b).

Preparation of glutathione Sepharose-RF fusion complexes: Strain BL21(DE3) pLysS transformed with pGEX2T, pGEX2T-SUP35 or pGEX2T-SUP45 (Paushkin et al. 1997b) were grown at 24° C. in LB with 50 µg/ml ampicillin and 30 µg/ml chloramphenicol to $OD_{600}$=0.6. 0.3mM IPTG was added and cells grown overnight. Cells were collected and washed once with cold TBST (50 mM Tris pH7.4, 150 mM NaCl, 0.1% TritonX-100) with 0.5 mM PMSF. Cells were resuspended in 50 µl of TBST with 0.5 mM PMSF per ml of culture and lysed by sonication. TritonX-100 was added to a final concentration of 1% and lysates mixed for 20 minutes at 4° C. Cell debris was removed by centrifugation at 30,000×g for 30 minutes. 80 µl of a 50% slurry of glutathione-sepharose (Pharmacia) equilibrated in TBST was added per ml of extract and incubated at 4° C. with mixing for 30 minutes. Sepharose beads were collected at 500×g for 3 minutes, washed for 3 minutes with TBST supplemented with NaCl to 500 mM and collected as before for a total of 2 times. The Sepharose-protein complexes were then washed and collected as before with IBTB (25 mM Tris-HCl pH 7.5, 50 mM KCl, 10 mM $MgCl_2$, 2% glycerol, 0.1% Triton x-100, 100 µg/ml BSA) for a total of 2 times, and resuspended in IBTB to yield a 2:1 ratio of buffer to packed bead volume. 1 µl of GST-RF complexes typically contained 0.9 µg GST-eRF1 or 1.5 µg GST-eRF3, while GST complexes typically contained 4.5 µg GST per µl of resin.

Preparation of cytoplasmic extracts: BJ3505 (MATβ pep4::HIS3 prb-Δ1.6R HIS3 lys2-208 trp1-Δ10 ura3-52 gal2 can1) cells were grown to an $OD_{600}$=1.0 and washed in 5 ml of cold Buffer IB (IBTB lacking BSA) with 0.5 mM PMSF. Cells were repelleted and suspended in 1.3 ml of cold IB with 0.5 mM PMSF and protease inhibitors (PI, 1 µg/ml each Leupeptin, Aprotinin and pepstatin A) per g of cell weight. An approximately equal volume of glass beads was added and lysis was achieved by vortexing 6 times for 20 seconds, with 1 minute cooling on ice in between vortexing. The lysate was removed, and the beads washed 2 times with an equal volume of IB with 0.5 mM PMSF and 1 µg/ml each Leupeptin, Aprotinin and pepstatin A. The washes were combined with the lysate and the cell debris was removed by centrifugation at 30,000×g for 20 min.

Preparation of [PSI$^+$] upf1Δ strains: UPF1 was deleted from [PSI$^+$] strain 7G-H66 (MATa ade2-1 SUQ5 trp1-289 lue2-3, 112 ura3-52 [PSI$^+$]) as described (Cui et al. 1995. The deletion was confirmed by Southern blot analysis. To cure the [PSI$^+$] determinant, 7G-H66 upf1Δ was grown in media containing 3 mM GuHCl (Ter-Avanesyan et al. 1994). Disruption of UPF1 resulted in suppression of ade2-1, which is used to monitor the suppressor phenotype of [PSI$^+$], therefore the [psi$^-$] status of clones obtained after growth on GuHCl medium was identified in crosses with the 1A-H19 [psi$^-$] tester strain (MATΔ ade2-1 lys2-1 his3-11,15 lue2-3, 112 SUQ5 [psi$^-$])(Ter-Avanesyan et al. 1994). The suppressor phenotype of the upf1Δ allele is a recessive trait while the [PSI$^-$] determinant is dominant. Therefore the non-suppressor phenotype of the diploids indicated [psi$^-$] state of the clones. The [PSI$^+$] and [psi$^-$] isolates of strain 7G-H66 upf1Δ were then transformed with the centromeric based plasmid YCplac22FLAGUPF1 (Weng et al. 1996a., Weng et al., 1996b).

Preparation of lysates for [PSI$^+$] aggregate co-centrifugation:7G-H66 upf1Δ cells transformed with YCplac22 or YCpFLAGUPF1 were grown in media lacking tryptophan to $OD_{600}$ =1.5, washed in water, and lysed by mixing with glass beads in Buffer A (25 mM Tris-HCL pH 7.5, 50 mM KCl, 10 mM $MgCl_2$, 1 mM EDTA, 2% glycerol) containing 1 mM PMSF and PI (2 µg/ml aprotinin, 1 µg/ml pepstatin A, 0.5 µg/ml leupeptin, 2.5 µg/ml antipain, 0.5 µg/ml TLCK, 0.5 µg/ml TPCK, 0.1 mM benzamidine, and 0.1 mM sodium metabisulfite). Lysates were centrifuged at 15,000×g for 20 minutes, then treated with RNaseA (400 µg/ml) to disrupt polyribosomes. Extracts were then subjected to centrifugation through a sucrose cushion as described previously (Paushkin et al. 1997b). Ribosomes migrate primarily to the sucrose fraction and since eRF1, eRF3 and Upf1p are all ribosome associated, they are present in this fraction in [psi$^-$] extracts.

Preparation of purified GST-RF fusion proteins: Extracts from 400 ml cultures of strain BL21(DE3) pLysS transformed with pGEX2T, pGEX2T-SUP35 or pGEX2T-SUP45 were prepared as described above for preparation of GST-RF fusion complexes. 800 µl of a 50% slurry of glutathione-Sepharose was added and incubated with mixing for 30 minutes. Sepharose beads were collected and washed 2 times for 3 minutes with TBST supplemented with NaCl to 500 mM, and collected by centrifugation at 500×g for 3 minutes. The sepharose beads were then washed in TBST and collected for a total of 2 times. GST fusion proteins were eluted by resuspending the washed sepharose beads in 400 µl glutathione elution buffer (10 mM Tris-HCl pH8.0, 1 mM glutathione) and incubating at room temperature for 10 minutes with mixing. Sepharose beads were collected and the supernatant removed. Elution was repeated as before for a total of 3 times, and the elution fractions combined. Concentration of proteins was determined by the Bradford assay.

Immunodetection of Upf1, eRF1 and eRF3: Upf1 was detected using the M2 mouse monoclonal antibody against the FLAG epitope as described previously (Czaplinski et al. 1995, Weng et al. 1996a,b). eRF3 was detected as described in Didichenko et al. 1991. eRF1 was detected as described in Stansfield et al. 1992.

ATPase assays:Upf1p RNA-dependent ATPase activity was determined using 20 ng Upf1p in the presence of GST-RF fusion proteins by a charcoal assay as described previously (Czaplinski et al. 1995) using 1 µg/ml poly(U) RNA with and 100 µg/ml BSA. The results are plotted as pmol of $^{32}P$ released versus the concentration of the indicated protein.

RNA binding assay: A uniformly labeled 32 nt RNA was synthesized by SP6 transcription of SstI digested pGEM5Zf (+) as described previously (Czaplinski et al. 1995). RNA binding buffer was as described previously (Czaplinski et al. 1995) with the exception that 100 µg/ml BSA was included in all reactions. The indicated amounts of GST-eRF3 (28), were incubated with 200 ng Upf1p for 15 minutes at 4° C. 50 fmol of the RNA substrate was added and incubated for 5 minutes. Stop solution was added, and reactions electrophoresed in a 4.5% native PAGE gel (0.5×TBE, 30:0.5 acrylamide:bisacrylamide, with 5% glycerol).

RESULTS

Upf1p interacts with the peptidyl release factors eRF1 and eRF3: Upf1p modulates translation termination by interacting with the peptidyl release factors eRF1 and eRF3. eRF1 and eRF3 were individually expressed in E. coli as glutathione-S-transferase (GST) fusion proteins and purified using glutathione sepharose beads. The purified GST-RF (release factor) fusion proteins associated with the glutathione sepharose beads were added to a yeast cytoplasmic extract containing a FLAG epitope-tagged Upf1p (Czaplinski et al. 1995, Weng et al. 1996a,b). Following incubation, the GST-RFs and associated proteins were purified by affinity chromatography and subjected to SDS-PAGE. Immunoblotting was performed and the presence of the Upf1p was assayed using an antibody against the FLAG epitope. The anti-FLAG antibody recognized only the 109 kD Upf1p in cytoplasmic extracts from cells transformed with plasmid expressing the FLAG-Upf1p (FIG. 1A, compare lane 2 to lane 1). This analysis also demonstrated that the Upf1p specifically co-purified with either eRF1 (FIG. 1A, lane 5) or eRF3 (FIG. 1A, lane 4). Upf1p did not co-purify with GST protein that was not fused to another protein (FIG. 1A, lane 3) or a GST-JIP protein, in which a Jak2 interacting protein fused to GST was used to monitor the specificity of the reaction.

The interaction of purified Upf1p with either eRF1 or eRF3 was also monitored. The purification for epitope tagged Upf1p (FLAG-Upf1p) has been described previously (Czaplinski et al. 1995). Purified FLAG-Upf1p was incubated with the GST-RF fusion proteins in the presence of increasing salt concentrations and the interactions of these proteins were monitored as described above. The results demonstrated that the purified FLAG-Upf1p interacted with either eRF1 or eRF3 (FIG. 1B, lanes 8–12 (eRF1) and lanes 3–7 (eRF3)). The Upf1p-eRF3 complex was less sensitive to increasing salt concentrations than the Upf1-eRF1 complex (FIG. 1B). The interactions were specific, since the purified Upf1p did not interact with the GST protein (FIG. 1B, lane 2) or GST-JIP. Interaction of Upf1p with either eRF1 or eRF3 was shown to be dose-dependent.

The Upf1p is associated with the aggregates of eRF3 in [PSI$^+$] strains: The biochemical results demonstrated that the Upf1p could enhance translation termination at a nonsense codon by interacting with the peptidyl release factors and enhancing their activity. Recent results have shown that the nonsense suppressor phenotype observed in strains carrying the cytoplasmically-inherited determinant [PSI$^+$] is a consequence of a specific alternative protein conformational state of the yeast eRF3 (Sup35p). In a [PSI$^+$] state, eRF3 forms high-molecular weight aggregates, or an amyloid-like fiber, which inhibit eRF3 activity, leading to increased readthrough of translation termination codons by ribosomes (Wickner, 1994; Paushkin et al. 1997a, Patino et al. 1996; Glover et al., 1997). It was also suggested that this specific alternative conformation of eRF3 is capable of self-propagation by an autocatalytic mechanism, analogous to that of mammalian prions (Paushkin et al. 1997a, Glover et al. 1997, Wickner, 1994). Thus, the alternative protein conformational state of the eRF3, and not a mutation in the SUP35 gene, allows self-propagation of the [PSI$^+$] phenotype. Yeast eRF1 (Sup45p) interacts with eRF3 and was also found in the aggregates present in [PSI$^+$] cells (Paushkin et al. 1997b).

Figure 2:
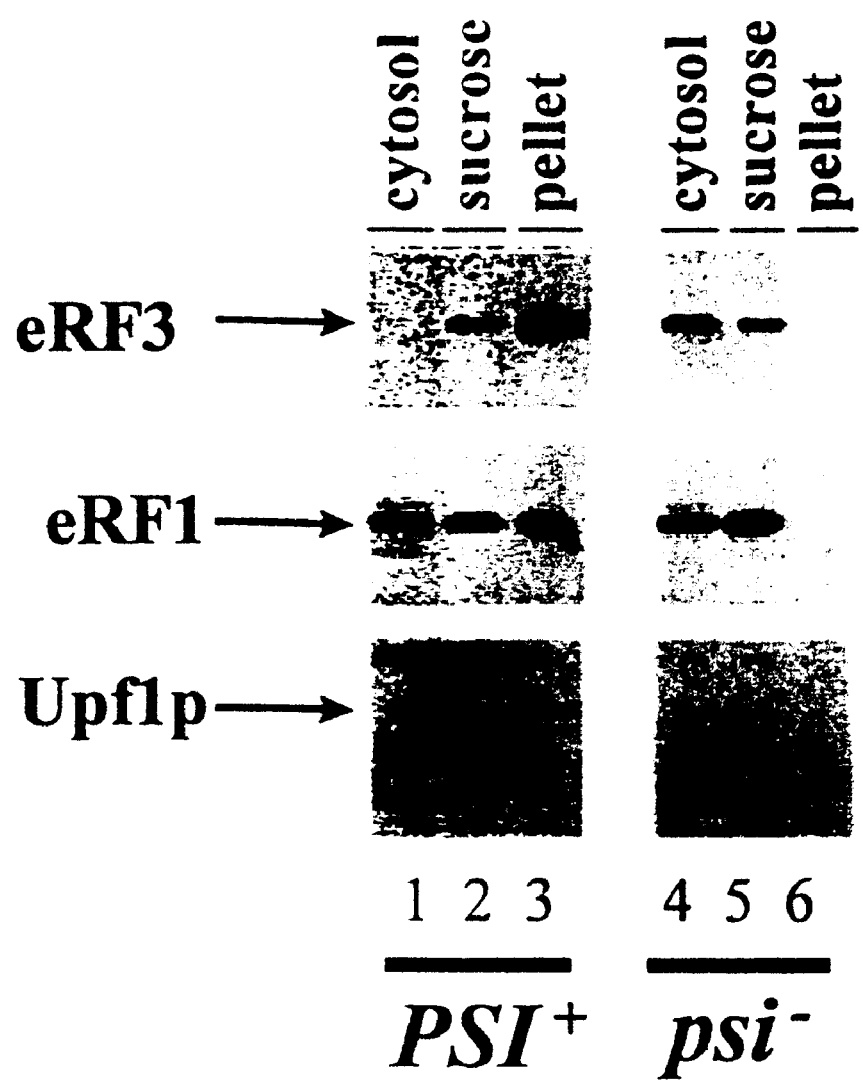
FIG. 2. The Upf1p is associated with eRF3 [PSI+] aggregates. Cytoplasmic extracts from isogenic [PSI+] and [psi−] variants of strain 7G-H66 upf1Δ and containing FLAG-UPF1 inserted into a centromere plasmid were fractionated by centrifugation through a sucrose cushion as described previously (Paushkin et al. 1997b). Supernatant (cytosol), sucrose pad (sucrose) and pellet fractions were subject to SDS-PAGE, and the distribution of eRF1 eRF3 and Upf1p within these fractions was determined by immunoblotting using polyclonal antibody against eRF1, and eRF3 and a monoclonal antibody against the FLAG epitope. A 95k-Da protein cross reacts with anti-FLAG antibody in strain 7G-H66, and has the same distribution in [PSI+] and [psi−] cells. This 95kD protein is not present in extracts prepared from strain BJ3505 (see FIG. 1).

It was reasoned that due to the interaction of Upf1p with eRF1 and eRF3, Upf1p may be associated with the eRF3 aggregates in [PSI$^+$] cells. To test this possibility, the presence of the Upf1p in the eRF3 and eRF1 aggregates found in [PSI$^+$] cells was monitored. Previous results demonstrated that the eRF1/eRF3 aggregates sedimented through a sucrose pad in extracts prepared from [PSI$^+$] cells. Cytoplasmic extracts from isogenic [psi$^-$] and [PSI$^+$] cells were prepared and centrifuged through a sucrose cushion and the presence of Upf1p, eRF1 and eRF3 was monitored in different fractions by western blotting analysis. The results demonstrated that Upf1p, eRF1 and eRF3 were present in the pellet fraction in extracts from [PSI$^+$] cells but were not found in the pellet fraction in a [psi$^-$] extract (FIG. 2, compare lanes 3 and 6). This result provides evidence that the Upf1p interacts with the translation termination factors in yeast cells.

eRF3 and RNA compete for interaction with Upf1p: Reaction mixtures were prepared containing purified FLAG-Upf1p and either purified GST-eRF1 or GST-eRF3 and containing either GTP, or poly(U) RNA. Following incubation, the sepharose-GST-RF fusion complexes were washed with the same buffer containing either GTP, or poly(U) RNA. The remaining bound proteins were subjected to SDS-PAGE followed by immunoblotting using an antibody against the FLAG epitope. The results demonstrated that the interaction between Upf1p and eRF3 was not affected by GTP (FIG. 3A, compare lane 3 to 4 and. A similar experiment showed that ATP did not affect the interaction between eRF3 and Upf1p (FIG. 3A, compare lane 3 to 5). Although poly(U) RNA did not affect the Upf1p-eRF1 interaction (FIG. 3B), the Upf1p-eRF3 interaction was dramatically reduced in reactions containing poly(U) RNA (FIG. 3A, compare lane 3 to 6).

The results described above indicated that RNA and eRF3 compete for binding to Upf1p. The effect of eRF3 on the ability of Upf1p to complex with RNA was monitored. Reaction mixtures containing Upf1p and RNA, and either lacking or containing increasing concentrations of eRF3, were prepared and the formation of the Upf1p:RNA complex was monitored by an RNA gel shift assay (Czaplinski et al. 1995, Weng et al. 1996a,b, Weng et al. 1998). Results suggest that RNA and eRF3 bind competitively to Upf1p.

Figure 4:
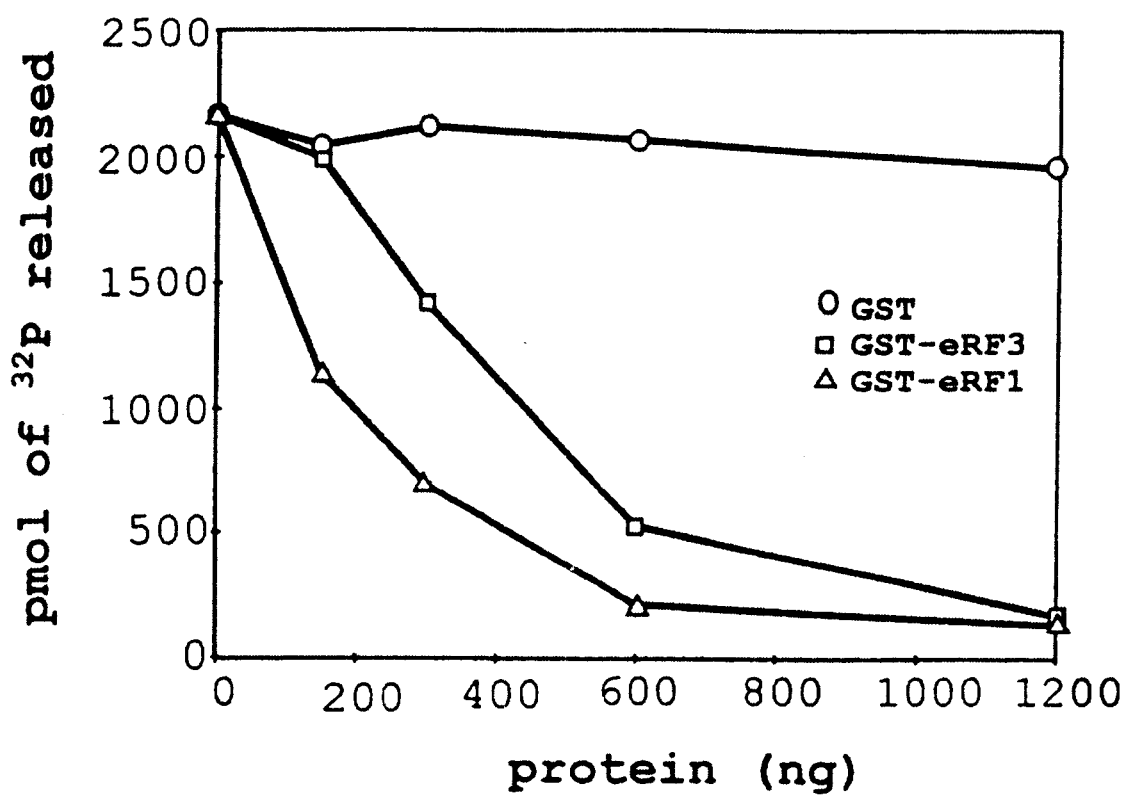
FIG. 4. eRF1 and eRF3 inhibit Upf1p RNA-dependent ATPase activity. Upf1p RNA-dependent ATPase activity was determined in the presence of GST-RF fusions by a charcoal assay using 1 μg/ml poly(U) RNA with and 100 μg/ml BSA. The results are plotted as pmol of $^{32}$P released versus the amount of the indicated protein.

Further, purified Flag-Upf1p with poly(U) RNA was incubated in the presence or absence of ATP. Following incubation, GST-eRF3 was added to the reaction mixtures and the Upf1-eRF3 interaction was monitored by immunoblotting analysis as before. The results demonstrated that when poly(U) and ATP were both present in the reaction mixture the Upf1p interacted with eRF3 with the same affinity as in reactions lacking poly(U) RNA (FIG. 4A, lanes 6, 8 and 10). Control experiments demonstrated that ATP did not prevent association of Upf1p with eRF3 (FIG. 4A Lane 4), and poly(U) RNA completely inhibited the interaction (FIG. 4A, lanes 5, 7 and 9). These results are consistent with the notion that ATP binding to Upf1p functionally enhances interaction of Upf1 with eRF3, by preventing binding of competing RNAs.

The K436A form of the Upf1p demonstrates altered interactions with the translation termination release factors: It was next determined whether a mutation in the UPF1 gene that inactivated its mRNA turnover and translation termination activities affected the ability of the Upf1p to interact with the translation termination release factors. Previous results have shown that strains harboring mutations in the conserved lysine residue in position 436 of the Upf1p (K436) result in stabilization of nonsense-containing mRNAs and a nonsense suppression phenotype (Weng et al., 1996a). Using a purified K436A form of the Upf1p (Weng et al., 1996a, 1998), it was questioned whether this mutation affected the ability of the Upf1p to interact with the eRF1. Reaction mixtures containing the K436A form of Upf1p, GST-eRF1 and various KCl concentrations were prepared, and their interaction was monitored as described above. The results demonstrated that the K436A mutation dramatically reduced the interaction of Upf1$_{K436A}$ with eRF1 at least 4 to 6 fold relative to the interaction of wild-type Upf1 with eRF1 (FIG. 4B, compare lanes 3 and 4 to lanes 7 and 8 and.

The ability of the K436A Upf1p to interact with eRF3 was monitored. A reaction mixture containing the K436A Upf1p and GST-eRF3 was prepared and the Upf1p-eRF3 interaction was monitored as described above. The result demonstrated that the mutant form of Upf1p was capable of interacting with eRF3 with an equivalent affinity as the wild-type Upf1p (FIG. 4C, lane 3).

The K436A mutation affected the ability of the Upf1p to preferentially interact with eRF3 versus RNA when ATP is present in the reaction mixture. The K436A mutation has been shown to reduce the affinity of the Upf1p for ATP (Weng et al., 1996a, 1998). However, although K436A form of the Upf1p is still capable of binding RNA, unlike the wild-type Upf1p, ATP is unable to dissociate the RNA:Upf1p$_{K436A}$ complex (Weng et al., 1996a, 1998). Therefore, the ability of the Upf1p$_{K436A}$ to interact with eRF3 in the presence of ATP and RNA was monitored. Reaction mixtures containing the mutant Upf1p and either ATP, poly(U) RNA, or ATP and poly(U) RNA were prepared and interaction of the Upf1p with eRF3 was monitored as described above. The results demonstrated that, analogous to the wild-type Upf1p, poly(U) RNA prevented the interaction of Upf1P$_{K436A}$ with eRF3 (FIG. 4C, lane 4). However, unlike the wild-type Upf1p, ATP was unable to restore interaction of Upf1P$_{K436A}$ with eRF3 in the presence of poly(U) RNA (FIG. 4C, lane 5). This result indicates that the Upf1P$_{K436A}$ will not favor the Upf1p-eRF3 complex over the Upf1p-RNA complex when ATP is present in the reaction. Taken together, these results suggest that strains harboring the K436A upf1 allele, which no longer degrades aberrant mRNAs and display a nonsense suppression phenotype, demonstrate altered interactions with the translation termination release factors. The altered Upf1P$_{K436A}$:eRF interactions observed in the in vitro reactions correlate well with the in vivo mRNA decay and nonsense suppression phenotypes of this mutant upf1 allele.

eRF1 and eRF3 inhibit Upf1p ATPase activity: The genetic and biochemical data indicated that the ATPase/helicase activities were not required for enhancing translation termination but were necessary to degrade nonsense-containing transcripts (Weng et al., 1996a,b; Weng et al., 1997). Based on these results, the interaction of the Upf1p with the eRFs was predicted to inhibit its ATPase/helicase activity, thus allowing the Upf1p to enhance translation termination. Therefore, the interaction of Upf1p with either eRF1 or eRF3 was examined if it would affect the RNA-dependent ATPase activity of Upf1p. Reaction mixtures were prepared containing radiolabeled $\gamma^{32}$P-ATP and either 1) Upf1p, 2) Upf1p and RNA, 3) Upf1p, RNA and GST, 4) Upf1p, RNA and GST-eRF1 or 5) Upf1p, RNA and GST-eRF3. The ATPase activity in these reactions was monitored using a charcoal assay as described previously (Czaplinski et al. 1995, Weng et al. 1996a, Weng et al. 1996b). The results demonstrated that reactions containing only Upf1p had no detectable ATPase activity while reactions containing Upf1p and poly(U) RNA demonstrated maximal ATPase activity. Addition of either eRF1 or eRF3 inhibited RNA-dependent ATPase activity of the Upf1p in a dose dependent manner (FIG. 5, GST-eRF1 and GST-eRF3). Addition of the GST protein to the reaction mixtures had no effect on the RNA dependent ATPase activity of the Upf1p (FIG. 5, GST). Neither eRF1 nor eRF3 demonstrated any intrinsic ATPase activity or stimulated the Upf1p ATPase activity in reactions lacking RNA. The inhibition of the Upf1p ATPase activity by eRF1 was not simply a consequence inhibiting its RNA binding activity, since eRF1 does not inhibit this function of Upf1p. Taken together, these results demonstrate that the ATPase activity of the Upf1p can be modulated by its interaction with the translation termination factors.

The yeast/human. UPF1 allele functions to modulate translation termination: It was determined whether the human homologue of the yeast Upf1p, called rent1 or hupf1 also modulated translation termination and mRNA turnover, suggesting a conserved role for this protein throughout evolution. The rent1/hupf1 in yeast cells (Perlick et al. 1996) was monitored. Therefore, it was questioned whether expression of a yeast/human UPF1 hybrid gene would prevent nonsense suppression in a upf1Δ strain and promote decay of aberrant transcripts. Although the amino and carboxyl terminal ends of the human and yeast Upf1p are divergent, the rent1/hupf1 contains both the cysteine/histidine-rich region and helicase motifs found in the yeast UPF1 gene and displays 60% identity and 90% similarity over this region (Perlick et al. 1996, Applequist et al. 1997). The hybrid construct used in these experiments consisted of the conserved domains from the human protein sandwiched between the N and C termini from the yeast UPF1 gene (Perlick et al. 1996). This hybrid gene was previously shown to complement a upf1Δ strain in a frameshift allosuppression assay (Perlick et al. 1996). It was initially asked whether expression of the hybrid gene would function to prevent nonsense suppression. To test this possibility, a upf1Δ strain harboring leu2-2 and tyr7-1 nonsense alleles was transformed with plasmids harboring either; 1) the vector alone, 2) the wild-type yeast UPF1 gene, or 3) the yeast/human hybrid gene expressed from a MET25 promoter inserted into either a centromere (YCpRENT1CHI4-2) or a high copy plasmid (YEpRENT1CHI4-2). Methionine was omitted from the media to increase the expression of the hybrid gene (Perlick et al. 1996). Suppression of the leu2-2 and tyr7-1 nonsense alleles was monitored by plating cells on —trp-met-leu-tyr media. As a control, these cells were plated on —trp-met media. The results demonstrated that the upf1Δ cells harboring the vector grew on both types of media (FIG. 6A), indicating suppression of these nonsense alleles. Cells harboring the yeast UPF1 gene were unable to grow on —trp-met-leu-tyr media demonstrating that the presence of the yeast UPF1 gene prevented suppression of these nonsense alleles (FIG. 6A). Similarly, expression of the hybrid yeast/human UPF1 gene prevented growth of these cells on —trp-met-leu-tyr media, demonstrating the ability of this protein to substitute for the yeast Upf1p in preventing suppression of the leu2-2 and tyr7-1 alleles (FIG. 6A). The hybrid gene functioned better when expressed from a multicopy plasmid (FIG. 6A). The expression of the chimeric protein had no effect on normal cell growth, since cells harboring these plasmids grew as well as wild-type on the —trp-met media (FIG. 6A).

Yeast/human UPF1 gene promotes decay of nonsense-containing transcripts in yeast cells. To test this, the abundance of the tyr7-1 and leu2-2 nonsense-containing transcripts were determined in a upf1Δ strain harboring either the vector plasmid, the yeast UPF1 gene, or the human/yeast hybrid UPF1 allele in a high copy plasmid. Total RNAs from these cells were isolated and the abundances of the tyr7 and leu2 transcripts were analyzed by RNA blotting analysis, probing the blots with radiolabeled DNA probes encoding the TYR7 and LEU2 genes (Weng et al. 1996a, Weng et al. 1996b). The results demonstrated that the leu2-2 and tyr7-1 mRNAs were low in abundance in a UPF1$^+$ cell but were abundant in both a upf1Δ strain and a upf1Δ containing the yeast/human hybrid allele (FIG. 6B). Similarly, the CYH2 precursor, which is an endogenous substrate for NMD (He et al. 1993). was abundant in cells expressing the yeast/human hybrid allele, while the CYH2 mRNA levels were similar in all 3Δ strains (FIG. 6B). Taken together, these results indicated that the product of the yeast/human UPF1 hybrid gene functions in translation termination but does not activate the NMD pathway in yeast cells.

Figure 7:
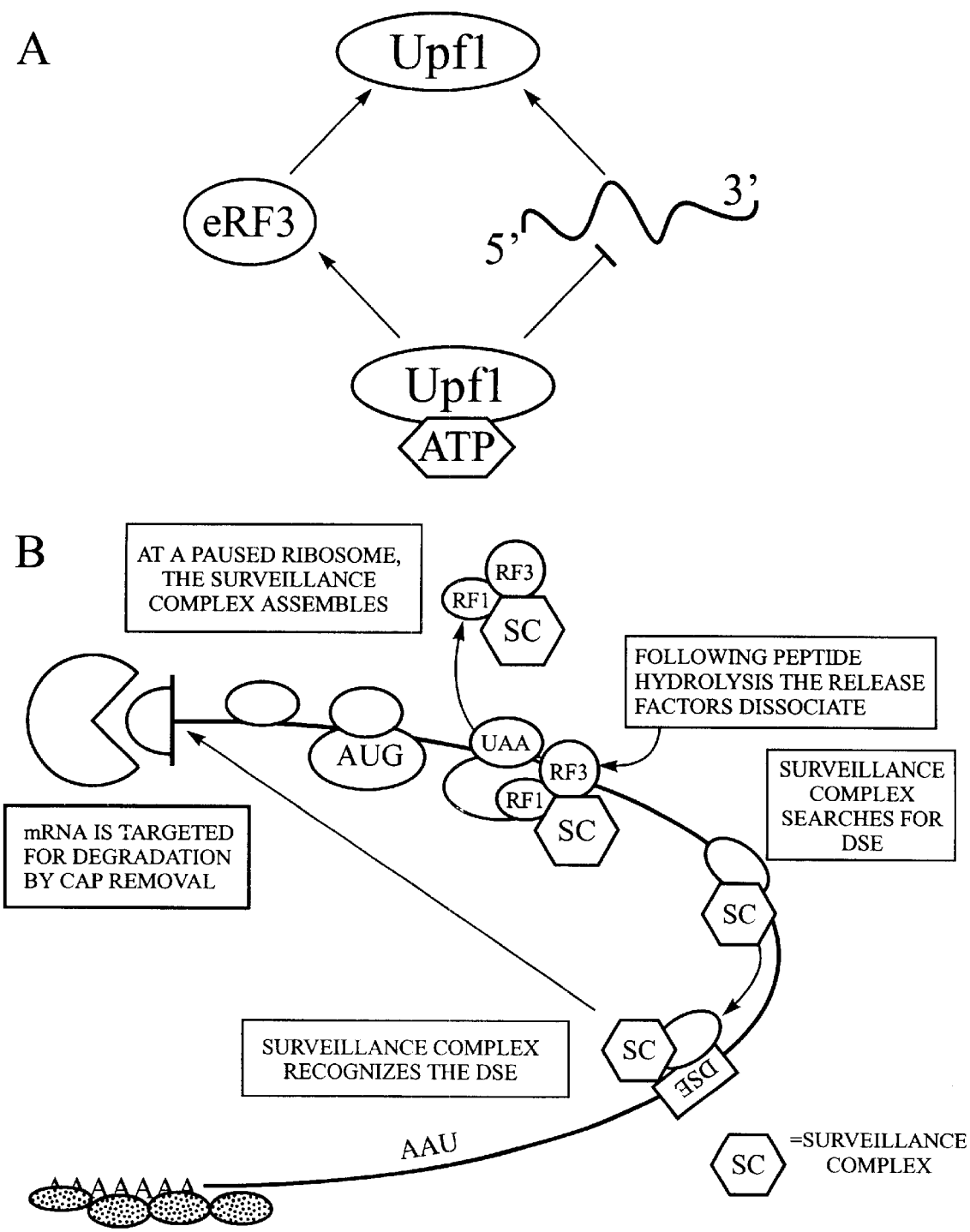

The human Upf1p interacts with the peptidyl release factors eRF1 and eRF3: The results described above demonstrate that the human homologue of the UPF1 gene may also function in modulating the translation termination activity of the peptidyl release factors. Therefore, it was asked whether the full length rent1/hupf1 would interact with eRF1 and eRF3. To test this possibility, radiolabeled rent1/hupf1 protein was synthesized in a coupled in vitro transcription/translation system. In vitro synthesis of the rent1/hupf1 produced a band of approximately 130 kD (FIG. 7 lane 1), consistent with the reported size of rent1/hupf1 (Applequist et al. 1997). The luciferase protein was also synthesized as described above and was used as a control protein for specificity of the interaction. Synthesis of the luciferase protein produced a 68 kd protein (FIG. 7 lane 5). The rent 1/hupf1 or the luciferase protein was incubated with either GST, GST-eRF1 or GST-eRF3 as described above and the interactions of rent1/hupf1 or luciferase with these proteins were monitored by SDS-PAGE followed by autoradiography. The results demonstrated that the rent1/hupf1 interacted with both the GST-eRF1 or GST-eRF3 (FIG. 7 lane 3 and 4). The interaction was specific, since rent1/hupf1 did not form a complex with GST protein (FIG. 7 lane 2). Further, the in vitro synthesized luciferase protein did not interact with GST, GST-eRF1 or GST-eRF3 (FIG. 7 lanes 6–8). Furthermore, poly(U)RNA prevented the interaction of hupf1/rent1 with eRF3. Taken together, these results indicate that the rent1/hupf1 also interacts with the peptidyl release factors eRF1 and eRF3 and the Upf1p in the surveillance complex and modulate translation termination.

DISCUSSION

Previous results indicated that the Upf1p is a multifunctional protein involved in enhancing translation termination at nonsense codons and in promoting decay of nonsense-containing transcripts (Weng et al., 1996a,b; Weng et al., 1998). The results presented here begin to elucidate how the Upf1p functions in enhancing translation termination. It was demonstrated that both the yeast and human forms of the Upf1p affect translation termination by interacting with the peptidyl release factors eRF1 and eRF3 and modulating their activity (FIG. 1). These results were substantiated by demonstrating that the Upf1p was also observed as part of the peptidyl release factor aggregates, or fibers, observed in [PSI+] yeast cells, and a mutant form of Upf1 has altered interactions with the release factors.

The interaction of the Upf1p with the peptidyl release factors suggest that the Upf1p enhances the activity of these factors: The finding that the Upf1p is also associated with the eRF3 aggregates found in [PSI+] cells is consistent with this protein interacting with the translation termination release factors in vivo (FIG. 2). This result suggests that a portion of the Upf1p that is normally utilized by the cell to enhance translation termination is depleted from the cellular pool in yeast [PSI+] cells. At present, the effect of removing this portion of the Upf1p on NMD is not known. The results presented here identify Upf1p as a component of the [PSI+] complexes and play a role in aggregate formation or maintenance.

The precise mechanism of how eRF1 and eRF3 promote termination when the A site of the ribosome is occupied by a termination codon has not been fully elucidated (reviewed in Buckingham et al., 1997). One suggestion is that eRF1 may structurally mimic a stem of a tRNA while eRF3 may mimic the function of EF-1α(Didichenko et al., 1991). The interaction of these two proteins at the ribosomal A site promote cleavage of the peptide associated with the tRNA in the P site (Zhouravleva et al., 1995). There are several steps in the termination process in which interaction of the release factors with Upf1p could be envisioned to enhance its translation termination efficiency. These include; 1) increasing the efficiency in which the eRFs compete with near cognate tRNAs and productively interact with the ribosome to promote termination, 2) the efficiency of the eRFs to promote peptidyl hydrolysis, 3) or increasing the recycling of the eRFs so that there is a larger free pool of these factors that can promote termination.

The role of the Upf1p in enhancing translation termination may be conserved throughout evolution:The human homologue of the yeast UPF1 gene has recently been isolated (Perlick et al. 1996; Applequist et al., 1996). Although the human gene contained amino and carboxyl terminal domains that were not present in the yeast UPF1 gene, the human gene contained the cysteine-histidine-rich region and the helicase motifs found in the yeast homologue (Perlick et al., 1996; Applequist et al., 1997). Further, expression of a yeast/human hybrid of the UPF1 genes functioned in a frameshift suppression assay when expressed in a upf1Δ strain (Perlick et al., 1996). The results presented here demonstrate that, analogous to the Upf1p, expression of the yeast/human UPF1 allele prevented the nonsense suppression phenotype observed in a upf1Δ strain harboring the nonsense-containing leu2-2 and tyr7-1 alleles (FIG. 6). Although the yeast/human hybrid was able to complement the translation termination phenotype of the yeast Upf1p, it did not promote rapid decay of nonsense-containing mRNAs (FIG. 6). Furthermore, consistent with a role in translation termination, the human rent1/hupf1 protein also interacted with the translation termination factors eRF1 and eRF3 (FIG. 6). These results, as well as the predominantly cytoplasmic localization of both the yeast Upf1p and rent1/hupf1 (reviewed in Jacobson and Peltz; 1996; see Applequist et al., 1996), are consistent with a role of this protein in modulating translation termination. Taken together, these results suggest that the role of the Upf1p in translation termination is likely to be conserved throughout evolution.

Interaction with the release factors modulates the biochemical activities of the Upf1p: The results demonstrate that interaction of Upf1p with the release factors inhibited its ATPase activity and prevented Upf1p from binding to RNA (FIGS. 3 and 5). These results are consistent with the previous biochemical and genetic results demonstrating that the Upf1p ATPase/helicase and RNA binding activities were required to promote NMD but were dispensable for its translation termination activity (Weng et al., 1996a,b; Weng et al., 1998). It was also shown that RNA and eRF3 compete for binding to Upf1p (FIG. 3). This result suggests that factors that reduce the Upf1p affinity for RNA would consequently favor binding to the release factors. It was previously demonstrated that binding of ATP to Upf1p reduces its affinity for RNA (Weng et al., 1996a, 1998). The results shown here demonstrated that ATP causes Upf1 to favor interaction with eRF3 over RNA (FIG. 4C, FIG. 8A). Based on these results, ATP is a cofactor of the Upf1p that allows it to switch between its translation termination and NMD activities. The results from the genetic and biochemical analysis of the Upf1p are consistent with this hypothesis (Weng et al., 1996a,b 1998). For example, a mutant form of the Upf1p that lacked ATPase activity but still bound ATP, was still functional in preventing translation termination (Weng et al. 1996a. 1998). Significantly, the binding of ATP to this mutant form of the Upf1p still modulated its RNA binding affinity (Weng et al. 1998). Furthermore, a mutant Upf1p$_{K436A}$, whose RNA binding activity could not be modulated by ATP, did not function in enhancing translation termination at a nonsense codon (Weng et al. 1996a, Weng et al, 1998). This Upf1p$_{K436A}$ also demonstrated a dramatically reduced interaction with eRF1 (FIG. 4B), and did- not interact with eRF3 in the presence of RNA and ATP (FIG. 4C).

Based on the model described above, the termination event is a key point in the assembly of the surveillance complex and leads to enhanced translation termination and degradation of nonsense-containing transcripts. Translation termination may also be an important event in regulating the stability or translation efficiency of wild-type transcripts. The 3'-untranslated regions of many transcripts encode regulatory elements that modulate the translation efficiency and/or stability of their respective mRNAs (reviewed in Ross. 1995; Jacobson and Peltz, 1996; Jacobson, 1996; Caponigro et al., 1995; Wickens et al., 1997). It is conceivable that the termination event is also6 the cue for the assembly of complexes that subsequently interact with the elements in the 3'-UTR that modulate their stability and/or translation efficiency. Interestingly, one subunit of the protein phosphatase 2A (PP2A) is the translation termination factor eRF1 (Andjelkovic et al., 1996). It is possible that one role of eRF1 is to bring the PP2A phosphatase into the ribosome at the termination event. The PP2A may be then positioned in the appropriate location to modulate the activity of factors that regulate the translation efficiency or stability of the given transcripts. Interestingly, this scenario is very similar to the how the NMD pathway function is perceived. The basic premise for both wild-type and NMD is that termination is a rate limiting event that pauses the ribosome and signals the assembly of complexes that regulate subsequent events in the life span of a given transcript. Interestingly, although the role of PP2A in translation has not been investigated, mutations in the SAL6 gene that encodes a phosphatase has been shown to promote suppression of nonsense mutations (Vincent et al., 1994). Clearly, further experimentation is required to test this hypothesis.

Example 2

The Upf3 Protein is a Component of the Surveillance Complex that Monitors both Translation and mRNA Turnover and Affects Viral Maintenance The nonsense-mediated mRNA decay (NMD) pathway functions to degrade aberrant mRNAs which contain premature translation termination codons. In *Saccharomyces cerevisiae*, the Upf1, Upf2 and Upf3 proteins have been identified as trans-acting factors involved in this pathway. Recent results have demonstrated that the Upf proteins may also be involved in maintaining the fidelity of several aspects of the translation process. Certain mutations in the UPF1 gene have been shown to affect the efficiency of translation termination at nonsense codons and/or the process of programmed −1 ribosomal frameshifting used by viruses to control their gene expression. Alteration of programmed frameshift efficiencies can affect virus assembly leading to reduced viral titers or elimination of the virus. Here it is demonstrated that the Upf1 protein functions to regulate programmed −1 frameshift efficiency. A upf3Δ strain demonstrates increased programmed −1 ribosomal frameshift efficiency which results in loss of ability to mantain the $M_1$ virus. In addition, the upf3Δ strain is more sensitive to the antibiotic paromomycin than wild-type cells and frameshift efficiency increases in a upf3Δ strain in the presence of this drug. Further, Upf3p is epistatic to Upf1p and Upf2p. Based on these observations and the fact that the mof4-1 allele of the UPF1 gene also affects NMD and programmed −1 ribosomal frameshift efficiency, it was demonstrathed that the Upfp proteins are part of a surveillance complex that functions to monitor translational fidelity and mRNA turnover.

MATERIALS AND METHODS

Materials, strains, plasmids, media, and general methods: Restriction enzymes were obtained from Boehringer Mannheim, New England Biolabs, and BRL. Radioactive nucleotides were obtained from either NEN or Amersham. The isogenic yeast strains used in this study are listed in Table 1. *E coli* DH5α was used to amplify plasmid DNA. Plasmids pF8 and pTI25 were previously described (Dinman. J. D., Icho. T., and Wickner, R. B. (1991)) and are shown in FIG. 7. Plasmid pmof4BE carrying the mof4-1 allele in a YCplac33 vector was as described (Cui, Y, K. W. Hagan, S. Zhang,. and Peltz, S. W. (1995)). Yeast media were prepared as described (Rose, M. D., Winston, F. and Hieter, P. (1990)). Yeast transformations were performed by the lithium acetate method (Schiestl, R. H., and Gietz, R. D. (1989)). Cytoductions of L-A and $M_1$ into rho-o strains were as described previously (Dinman, J. D., and Wickner, R. B. (1992)) using strains 3164 and 3165 (Dinman, J. D. and Wickner, R. B. (1994); Dinman, J. D., and Wickner, R. B. (1992)) as cytoduction donors. β-galactosidase (β-gal) assays followed standard protocols (Guarente, L. (1983)).

Cloning of UPF3: The strategy used to clone the UPF3 gene was the same that was used to clone UPF2 (Cui, Y, K. W. Hagan, S. Zhang, and Peltz, S. W. (1995)). Subsequent subcloning revealed that a 2.1 kb Asp 718-Bgl II fragment was sufficient to complement upf3 mutations, and sequence analysis of this clone showed that it was identical to the UPF3 sequence previously reported (Lee, B. S., and Culbertson, M. R. (1995)). Killer assays, frameshifting assays and extraction and analysis of total nucleic acids: The killer assay was carried out as previously described (Dinman, J. D., and Wickner, R. B. (1992)) by replica plating colonies onto 4.7 MB plates newly seeded with a lawn of 5×47 killer indicator cells (0.5 ml of a suspension at 1 unit of optical density at 550 nm per ml per plate). After 2 days at 20° C., killer activity was observed as a zone of growth inhibition around the killer colonies. To quantitate loss of killer activity, colonies that had been identified as killer[+] were re-streaked for single colonies and the percentage of killer[+] colonies were determined. The efficiencies of −1 frameshifting were determined as previously described (Cui, Y. Dinman, J. D., and Peltz, S. W. (1996); Dinman, J. D., Ruiz-Echevarria, M. J., Czaplinski, K. and Peltz, S. W. (1 997b)) using the 0-frame control (pTI25) and −1 reporter (pF8) plasmids.

Total nucleic acids (TNA) were extracted from cells as previously described (Dinman. J. D. and Wickner, R. B. (1994); Dinman, J. D. and Wickner, R. B. (1992)). Equal amounts of TNA were separated through 1.0% agarose gels and visualized with ethidium bromide. TNA was denatured in the gels at 45° for 30 min in 50% formamide, 9.25% formaldehyde, 1×TAE, the gels were washed with water and nucleic acids were transferred to nitrocellulose. Extraction and of mRNAs were as previously described (Cui, Y., Dinman, J. D., and Peltz, S. W. (1996)). The abundance of L-A and $M_1$ (+) strand RNA were monitored as described (28). RNA abundance of the lacZ −1 frameshift reporter mRNA and U3 snRNA was determined by ribonuclease protection assays essentially as described (Sambrook).

Preparation of radioactive probes:For the ribonuclease protection assays, RNA probes were labelled with [α-$^{32}$P] UTP. To monitor the lacZ mRNA abundance, a pGEM derived plasmid containing the LacZ gene was digested with HincII and in vitro transcribed with RNA polymerase T7. To monitor the abundance of the U3 transcript, pGEM-U3, a pGEM-derived plasmid, was cut with Ssp1 and in vitro transcribed with RNA polymerase T3. L-A and $M_1$ (+) strand RNA probes were made as previously described using [$\alpha^{32}$P]CTP labeled T3 RNA polymerase runoff transcripts (28).

RESULTS

A upf3Δ strain demonstrates an increased efficiency of programmed −1 ribosomal frameshifting: mof4-1 is a unique allele of the UPF1 gene that specifically increases programmed −1 ribosomal frameshifting efficiency and promotes loss of the $M_1$ satellite virus. A upf1Δ strain, however, does not demonstrate these phenotypes. Other factors of the putative surveillance complex, including the Upf2 or Upf3 proteins, also affect programmed −1 ribosomal frameshifting. Therefore, isogenic strains harboring deletions of the UPF genes were investigated which demonstrated increased ribosomal frameshifting efficiencies.

Methods to measure efficiencies of programmed ribosomal frameshifting in vivo have been described previously (Cui, Y., Dinman, J. D., and Peltz, S. W. (1996); Dinman, J. D., Icho, T., and Wickner, R. B. (1991); Dinman, J. D., Ruiz-Echevarria, M. J., Czaplinski, K. and Peltz, S. W. (1997b)). A series of lacZ reporter plasmids were used in which transcription is driven from the yeast PGK1 promoter and terminates at the PGK1 polyadenylation site. A translational start codon is followed by a multiple cloning site, followed by the *E. coli* lacZ gene. Plasmid pTI25 serves as the 0-frame control since the lacZ is in the 0-frame with respect to the translational start site (FIG. 8). In plasmid pF8, an L-A derived programmed −1 ribosomal frameshift signal is cloned into the polylinker and the lacZ gene is in the −1 frame with respect to the translational start site (FIG. 8). Therefore, in this construct, the lacZ gene will be translated only if the ribosome shifts frame in the −1 direction. The +1 frameshift reporter plasmid, pJD104 (FIG. 8), contains the lacZ gene inserted 3' of a programmed +1 ribosomal frameshift signal derived from the Ty1 retrotransposable element of yeast. In this construct, the lacZ gene will be translated only if the ribosome shifts frame in the +1 direction. The efficiency of −1 ribosomal frameshifting is calculated by determining the ratio of β-gal activities measured in cells harboring the −1 frameshift reporter plasmid, pF8, to those harboring the 0-frame control plasmid, pTI25, and multiplying by 100%. Similarly, the +1 ribosomal frameshift efficiency is calculated based on the pJD104 to pTI25 β-gal ratios. These experiments were performed in isogenic yeast strains harboring deletions of different UPF genes, to avoid strain specific differences (Table 1).

TABLE 1

Strains used in this study

| Strain | Genotype | Reference |
|---|---|---|
| HFY1200 | MATa ade2-1 his3-11,15 leu2-3,112 trp1-1 ura3-1 can1-100 UPF1 NMD2 UPF3 | He et al., 1997 |
| HFY870 | MATa ade2-1 his3-11,15 leu2-3,112 trp1-1 ura3-1 can1-100 upf1::HIS3 NMD2 UPF3 | He et al., 1997 |
| HFY1300 | MATα ade2-1 his3-11,15 leu2-3,112 trp1-1 ura3-1 can1-100 UPF1 nmd2::HIS3 UPF3 | He et al., 1997 |
| HFY861 | MATa ade2-1 his3-11,15 leu2-3,112 trp1-1 ura3-1 can1-100 UPF1 NMD2 upf3::HIS3 | He et al., 1997 |
| HFY3000 | MATα ade2-1 his3-11,15 leu2-3,112 trp1-1 ura3-1 can1-100 upf1::URA3 nmd2::HIS3 UPF3 | He et al., 1997 |
| HFY872 | MATa ade2-1 his3-11,15 leu2-3,112 trp1-1 ura3-1 can1-100 upf1-1::URA3 NMD2 upf3::HIS3 | He et al., 1997 |

TABLE 1-continued

Strains used in this study

| Strain | Genotype | Reference |
|---|---|---|
| HFY874 | MATa ade2-1 his3-11,15 leu2-3.112 trp1-1 ura3-1 can1-100 UPF1 nmd2::URA3 upf3::HIS3 | He et al., 1997 |
| HFY883 | MATa ade2-1 his3-11,15 leu2-3,112 trp1-1 ura3-1 can-100 upf1::LEU2 nmd2::URA3 upf3::HIS3 | He et al., 1997 |
| HYF870mof4 | MATa ade2-1 his3-11,15 leu2-3,112 trp1-1 ura3-1 can1-100 upf1::HIS3 NMD2 UPF3 pmof4BE | This study |
| HFY872mof4 | MATa ade2-1 his3-11,15 leu2-3,112 trp1-1 ura3-1 can1-100 upf1-1::URA3 NMD2 upf3::HIS3 pmof4BE | This study |
| 3164 | MATa kar1-1 arg1L-AHN M1 K+ | Dinman and Wickner, 1992 |
| 3165 | MATα kar1-1 arg1 thr(1,x) L-AHN M1 K+ | Dinman and Wickner, 1994 |
| 5X47 | MATa/MATα his1/+trp/+ura3/+K⁻R⁻ | Dinman and Wickner, 1992 |

The results of these experiments demonstrated that the levels of β-gal activity, and therefore the apparent efficiency of programmed −1 ribosomal frameshifting, were slightly greater in upf1Δ and upf2Δ strains, 1.8 and 1.5-fold respectively, than in wild-type cells (Table 2). As will be discussed below, the small increase in −1 programmed frameshifting was not sufficient to promote loss of the $M_1$ virus. In contrast, the efficiency of programmed −1 ribosomal frameshifting in upf3Δ cells was 3.4-fold higher than wild-type cells (Table 2) and was sufficient to promote loss of the $M_1$ virus (see below). This result suggests that, analogous to a mof4-1 strain, a upf3Δ strain demonstrated an increased level of programmed −1 ribosomal frameshifting.

TABLE 2

Programmed −1 Ribosomal Frameshifting and $M_1$ Virus Maintenance of Strains Harboring a Single Deletion of a UPF Gene

| Strain (Genotype) | % −1 Ribosomal Frameshifting[a] | Killer Maintenance[b] |
|---|---|---|
| UPF+ (HFY1200) | 2.5 | + |
| upf1Δ (HFY870) | 4.5 | + |
| upf2Δ (HFY1300) | 3.9 | + |
| upf3Δ (HFY861) | 8.4 | − |

[a]The −1 ribosomal frameshift efficiency (%) was determined by the ratio of β-galactosidase activity in a strain harboring the −1 ribosomal frameshifting reporter plasmid to the activity in the same strain harboring the 0 frame control plasmid. [b]L-AHN and $M_1$ were introduced into the strains by cytoductionand the maintenance (+) or loss (−) of $M_1$ dsRNA was analyzed by the killer plate assay and Northern blot analyses as described in Material and Methods.

Interestingly, none of the mutant strains demonstrated a dramatic increase in the apparent efficiency of programmed +1 ribosomal frameshifting, as measured by the levels of β-galactosidase activity. Taken together, these results indicated that the upf3Δ strain specifically alter −1 ribosomal frameshifting.

The abundance of the frameshift reporter transcript is equivalent in the upfΔ strains: The −1 frameshift reporter transcripts used in these assays have short protein coding regions 5' of the frameshift site followed by sequences that code for a reporter protein and that is out of frame with the translation initiation site of the 5' open reading frame. The apparent changes in ribosomal frameshifting efficiencies could result from changes in the abundance of the LacZ −1 frameshift reporter mRNA which the translational machinery may recognize as a nonsense-containing mRNA. Deletion of the UPF genes could lead to stabilization of the −1 frameshift reporter transcript, resulting in increased synthesis of the β-gal reporter protein. To address whether a upf3Δ strain accumulates the reporter transcript to a greater extent than upf1Δ or upf2Δ strains, the abundance of the lacZ −1 frameshift reporter mRNA was determined by RNase protection analysis. As a loading control, it was determined the abundance of the U3 snRNA. Quantitation of the hybridizing bands revealed that the abundances of the lacZ frameshift reporter mRNA, normalized to the U3 snRNA, were equivalent in isogenic wild-type, upf1Δ, upf2Δ and upf3Δ strains (FIG. 9). Therefore, these results indicated that the increased programmed −1 ribosomal frameshifting efficiency observed in a upf3, when compared to the upf1Δ or upf2Δ strains, was not a consequence of stabilizing the reporter transcript to a greater extent than in the other upfΔ strains. The modest increase in the abundance of the −1 LacZ mRNA could not account for the four-fold increase in production of the β-gal reporter protein observed in a upf3Δ strain. Therefore, a upf3Δ also demonstrates a mof phenotype in that it increases the efficiency of −1 ribosomal frameshifting independent of its ability to stabilize nonsense mRNAs.

The $M_1$ killer virus is not maintained in a upfΔ strain: Changing the efficiency of −1 ribosomal frameshifting alters the ratio of Gag to Gag-pol proteins available for viral particle assembly, consequently interfering with viral propagation (Cui, Y., Dinman, J. D., and Peltz, S. W. (1996); Dinman, J. D. and Wickner, R. B. (1994); Dinman, J. D., and Wickner, R. B. (1992); Dinman, J. D., Ruiz-Echevarria, M. J., Czaplinski, K. and Peltz, S. W. (1997b)). The L-A and $M_1$ viruses were introduced by cytoduction into isogenic wild-type UPF+, upf1Δ, upf2Δ and upf3Δ strains, and these cells were grown and replica plated onto a lawn of cells sensitive to the killer toxin. Cells maintaining the $M_1$ virus secrete the killer toxin, creating a ring of growth inhibition, whereas cells which have lost $M_1$ do not demonstrate this growth inhibition (Cui, Y., Dinman, J. D., and Peltz, S. W. 1996); Dinman, J. D., and Wickner, R. B. (1992); Dinman, J. D., Ruiz-Echevarria, M. J., Czaplinski, K. and Peltz, S. W. (1997b)). The results of this assay demonstrated that the wild-type, upf1Δ and upf2Δ strains maintained the killer phenotype, while the upf3Δ strain loose the ability to mantain the killer phenotype (FIG. 10A; Table 2). Consistent with previous results, cells harboring the mof4-1 allele were also unable to mantain the killer phenotype (Cui, Y., Dinman, J. D., and Peltz, S. W. (1996)).

To determine whether lack of the killer phenotype was a consequence of a virus maintenance defect rather than interference with production of the killer toxin, total nucleic acids were extracted from a colony of each one of the UPF+, upf1Δ, upf2Δ and upf3Δ strains, and equal amounts of nucleic acids were separated in a non-denaturing agarose gel. The RNAs were transferred to nitrocellulose and hybridized with [α-$^{32}$P]CTP labeled L-A and $M_1$ (+) strand RNA specific probes. The results are shown in FIG. 10B. Consistent with the loss of killer phenotype, the 1.8 kb $M_1$ ds RNA was absent in the mof4-1 and upf3Δ cells but present in upf1 and upf2 mutants and the wild-type strains. These results support the hypothesis that deleting the UPF3 gene alters the efficiency of −1 ribosomal frameshifting interfering with the propagation of $M_1$ satellite virus.

The upf3Δ strain demonstrates increased sensitivity to paromomycin: Strains harboring mutations that diminish translational fidelity are hypersensitive to the aminoglycoside antibiotic paromomycin, a drug that is thought to increase the frequency of misreading in yeast. Previous results demonstrated that cells harboring the mof4-1 allele of the UPF1 gene, which increases the efficiency of −1 ribosomal frameshift, also showed an increased sensitivity to paromomycin than the isogenic wild-type strain. It was determined whether a upf3Δ strain also demonstrates increased sensitivity to this antibiotic. Paromomycin sensitivity was monitored in isogenic wild-type and upf3Δ strains by placing a disc containing 1 mg of paromomycin onto a lawn of cells and determining the zone of growth inhibition around the disc (FIG. 11). The results demonstrate that, analogous to a mof4-1 strain, a upf3Δ strain was more sensitive to paromomycin than the isogenic wild-type strain. Neither the upf1Δ or upf2Δ strains demonstrate hypersensitivity to paromomycin.

The effect of paromomycin on −1 ribosomal frameshifting was analyzed further by β-galactosidase assay using plasmids pF8 (−1 frameshift reporter construct) or pTI25 (zero frame control) in isogenic wild-type and upf3Δ strains. Cells were grown in liquid media in the presence of different concentrations of the drug and the β-galactosidase activity was determined, normalizing to the number of cells used in the assay. The β-galactosidase activity from upf3Δ cells carrying pF8 (−1 frameshift reporter construct) increased continuously with increased concentrations of paromomycin. However, the β-galactosidase activity was unaffected in wild-type cells containing pF8 or in any of the strains carrying pTI25 (zero frame control construct). Taken together, these results indicate that paromomycin can augment the effect that deletion of the UPF3 gene has on the efficiency of −1 ribosomal frameshifting.

The increased −1 programmed frameshifting and killer virus maintenance defect phenotypes of upf3Δ and upf3Δ mof4-1 strains are equivalent: The results described above indicate that a upf3Δ strain has similar phenotypes as mof4-1 cells. Since the mof4-1 allele of the UPF1 gene, but not deletion of the UPF1 gene, affected programmed −1 ribosomal frameshifting and $M_1$ maintenance, we hypothesized that the mof4-1p could alter the function of the Upf3p. Thus, a mof4-1 upf3Δ strain should have the same programmed −1 frameshifting and killer phenotypes as a upf3Δ strain. The programmed −1 ribosomal frameshifting efficiency and virus maintenance phenotypes in isogenic mof4-1, upf3Δ and mof4-1 upf3Δ strains was monitored as described above. The results of this experiment are summarized in Table 3. The programmed −1 ribosomal frameshifting efficiencies observed in mof4-1, upf3Δ and mof4-1 upf3Δ strains were equivalent. Furthermore, all these strains lacked the killer phenotype (Table 3). These results suggest that the mof4-1 allele of the UPF1 gene alters programmed −1 ribosomal frameshifting by modulating the activity of the Upf3p.

The programmed frameshifting and killer phenotypes of a upf3Δ allele are independent of the other upfΔ alleles: The epistatic relationships between upf1Δ, upf2Δ and upf3Δ were examined with regard to both −1 ribosomal frameshifting efficiencies and killer maintenance. Both programmed −1 ribosomal frameshifting and killer phenotypes were monitored as described above in isogenic UPF−, upf1Δ upf2Δ, upf1Δ upf3Δ, upf2Δ upf3Δ and upf3Δ upf2Δ upf3Δ strains. The results of these experiments are shown in Table 3. All of the strains harboring the upf3Δ had increased efficiencies of −1 ribosomal frameshifting, equivalent to that harboring deletion of the UPF3 gene only, independent of the status of the UPF1 of UPF2 genes (Table 3). Conversely, upf1Δ UPF3⁺, upf2Δ UPF3⁺ and upf1Δ upf2Δ UPF3⁺strains did not demonstrate an increase in programmed −1 frameshifting efficiencies sufficient to promote loss of the killer phenotype (Table 2 and 3). Taken together, these results indicate that the Upf3p acts upstream of both the Upf1p and Upf2p.

DISCUSSION

The Upf proteins are part of the surveillance complex that monitors both mRNA turnover and translation. The NMD pathway is an example of a mechanism that the cell has evolved to rid itself of aberrant nonsense-containing transcripts which, when translated, could produce anomalous peptides that can dominantly interfere with the normal cellular functions (Jacobson, A. and Peltz. S. W. (1996); Ruiz-Echevarria, M. J., K. Czaplinski, and Peltz, S. W. (1996); Weng, Y., M. J. Ruiz-Echevarria, S. Zhang, Y. Cui, K. Czaplinski, J. Dinman, and S. W. Peltz. (1997); He, F., Peltz, S. W., Donahue, J. L., Rosbasch, M. and Jacobson, A. (1993); Pulak, R. and Anderson, P. (1993)). Interestingly, the clinical manifestation and severity of several human genetic diseases that are a consequence of nonsense-mutations can increase under conditions in which the nonsense-containing transcript is stabilized (Hall, G. W., and Thein, S. (1994); Dietz, H. C., I. McIntosh, L. Y. Sakai, G. M. Corson, S. C. Chalberg, R. E. Pyeritz, and Francomano, C. A. (1993); Dietz, H. C., U. Franke, H. Furthmayr, C. A. Francomano, A. De Paepe, R. Devereux, F. Ramirez, and Pyeritz, R. E. (1995)). The fact that every eucaryotic organism studied so far has maintained the NMD pathway, as well as the conservation in human cells of at least one factor involved in this process (Perlick, H. A., Medghalchi, S. M., Spencer, F. A., Kendzior, R. J. Jr., and Dietz, H. C. (1996); Applequist, S. E., Selg, M., Roman, C., and Jack, H. (1997)), suggests that the pressure to eliminate anomalous mRNAs is sufficient to maintain this process throughout evolution.

Recent results indicate that the factors involved in the NMD pathway play additional roles in modulating several aspects of the translation process. Genetic studies of the Upf1p suggest that it. is a multifunctional protein that acts both in NMD and in modulating the translation termination process (Weng, Y., K. Czaplinski, and Peltz, S. W. (1996a); Weng, Y., K. Czaplinski, and Peltz, S. W. (1996b)). More recent biochemical evidence indicates that the Upf1p interacts with the translation termination release factors eRF1 and eRF3. The function of the Upf1p in modulating translation termination is not surprising, since the NMD pathway functions by monitoring whether translation termination has aberrantly occurred and then degrading the anomalous mRNA.

The mof4-1 allele of the UPFI gene demonstrates an increase in programmed −1 ribosomal frameshifting efficiency and is unable to mantain the M₁ killer virus (Cui, Y., Dinman, J. D., and Peltz, S. W. (1996)). In addition, mo 2-1 mutants manifest increased programmed −1 ribosomal efficiency (Cui, Y., Dinman, J. D. D., Goss Kinzy, T. and Peltz, S. W. (1997)). The mof2-1 mutant is allelic to the SUI1 gene (Cui. Y., Dinman, J. D. D., Goss Kinzy, T. and Peltz, S. W. (1997)), which was previously shown to play a role in translation initiation start site selection. Interestingly, mof2-1 mutant strains also demonstrate accumulation of nonsense-containing. These results suggest that the surveillance complex, including factors involved in NMD, may also be involved in monitoring other steps in the translation process. The results presented here indicate that the Upf3p, in addition to its role in NMD, is part of the putative surveillance complex involved in maintaining appropriate translational reading frame. The results also suggest that the effect of the mof4-1 allele of the Upf1p in −1 ribosomal frameshifting most likely occurs through modulating the interactions of the Upf3p with the translational apparatus.

The Upf3p is the key factor that links the Upfp complex to programmed −1 ribosomal frameshifting. Monitoring the programmed ribosomal frameshifting and M₁ virus maintenance profiles of cells harboring deletions of the UPF1, UPF2 or UPF3 genes demonstrated that a upf3Δ strain affected programmed −1 frameshift efficiency and virus maintenance (Tables 2 and 3). The increased programmed −1 ribosomal frameshifting in a upf3Δ strain is not a consequence of stabilizing the reporter transcript to a greater degree than that observed in either upf1Δ or upf2Δ strains (FIG. 9). Consistent with this, the efficiency of −1 ribosomal frameshifting in upf3Δ cells was elevated in response to increasing doses of paromomycin, a drug known to affect translational fidelity. The observation that the mof4-1 allele of the UPF1 gene, but not a upf1Δ allele, affected programmed −1 ribosomal frameshifting and killer maintenance suggested that Upf1p does not directly influence the maintenance of the translational reading frame. The notion that the Upf3p is the central component of the Upfp complex that modulates programmed frameshifting is supported by the observation that a mof4-1 upf3Δ strain has the same programmed −1 ribosomal frameshift and killer phenotypes as a mof4-1 strain (Table 2).

The results presented here indicate that the Upf3p has a function in ensuring appropriate maintenance of translational reading frame. The function of the Upf3p in this process appears to be genetically epistatic to the Upf1p and Upf2p, since the programmed −1 frameshifting and killer maintenance phenotypes of a upf3Δ are observed in upf1Δ and upf2Δ strains (Table 3). Although the precise biochemical function of the Upf3p in this process is not known, the results presented here demonstrate that the Upfp's may have distinct roles that can affect different aspects of the translation and mRNA turnover processes. Importantly these results may also have practical implications, since many viruses of clinical, veterinary and agricultural importance utilize programmed frameshifting (reviewed in Brierley, I. (1995); Dinman, J. D. D., Ruiz-Echevarria, M. J. and Peltz, S. W. (1997)). Thus, programmed ribosomal frameshifting serves as a unique target for antiviral agents, and the identification and characterization of the factors involved in this process will help to develop assays to identify these compounds (Dinman, J. D. D., Ruiz-Echevarria, M. J. and Peltz, S. W. (1997)).

TABLE 3

Programmed −1 Ribosomal Frameshifting and M₁
Virus Maintenance of Strains Harboring Multiple
Mutations of UPF Genes

| Genotype (Strain) | % Ribosomal Frameshifting[a] | Killer Maintenance |
|---|---|---|
| UPF⁺ (HFY1200) | 2.5 | + |
| upf3Δ (HFY861) | 8.4 | − |
| (mof4-1 | 7.0 | − |

TABLE 3-continued

Programmed −1 Ribosomal Frameshifting and $M_1$
Virus Maintenance of Strains Harboring Multiple
Mutations of UPF Genes

| Genotype (Strain) | % Ribosomal Frameshifting[a] | Killer Maintenance |
|---|---|---|
| (HFY870mof4) mof4-1 upf3Δ (HFY872mof4) | 8.0 | − |
| upf1Δupf2Δ (HFY3000) | 3.2 | + |
| upf1Δupf3Δ (HFY872) | 7.2 | − |
| upf2Δupf3Δ (HFY874) | 9.2 | − |
| upf1Δupf2Δupf3Δ (HFY883) | 8.0 | − |

[a]Programmed −1 ribosomal frameshifting efficiency and $M_1$ virus maintenance was determined as described in the legend of Table 2.

As described above, mutations in the UPF genes can result in altered translation termination phenotypes, increased programmed frameshifting and stabilization of nonsense-containing transcripts (Weng, Y., K. Czaplinski, and Peltz, S. W. (1996a); Weng, Y., K. Czaplinski, and Peltz, S. W. (1996b); Cui, Y., Dinman, J. D., and Peltz, S. W. (1996).; reviewed in Ruiz-Echevarria, M. J., K. Czaplinski, and Peltz, S. W. (1996); Weng, Y., M. J. Ruiz-Echevarria, S. Zhang, Y. Cui, K. Czaplinski, J. Dinman, and S. W. Peltz. (1997)). Thus, although the products of these genes were initially thought to be solely involved in degrading aberrant mRNAs, the emerging picture indicates that the factors involved in this pathway play multiple roles in several aspects of translation (including translation elongation and termination) and mRNA turnover (Weng, Y., K. Czaplinski, and Peltz, S. W. (1996a); Weng, Y., K. Czaplinski, and Peltz, S. W. (1996b); Cui, Y., Dinman, J. D., and Peltz, S. W. (1996)). This demonstrates that the Upfp complex is part of a surveillance complex, functions as a "translational checkpoint". Analogous to cell cycle control checkpoints, the UPF genes are not essential, but ensure that the processes that they are involved in occur with high fidelity. In the absence of these factors, a subset of the translation and mRNA turnover processes are allowed to proceed less accurately.

A paused ribosome may be a key event that promotes assembly of the Upfp complex, which can subsequently monitor these processes. Both programmed frameshifting and translation termination involve a ribosomal pause (Wolin, S. L. and Walter, P. (1988); Tu, C., Tzeng, T.-H. and Bruenn, J. A. (1992); reviewed in Tate, W. P. and Brown, C. M. (1992)). The results show that the interaction of the translation termination release factors eRF1 and eRF3 with a paused ribosome containing a termination codon in the A site helps promote the assembly of the Upfp complex. The results show that the interaction of the Upfp complex with the release factors leads to enhanced translation termination and subsequent degradation of nonsense-containing transcripts. In the case of programmed −1 ribosomal frameshifting, the RNA pseudoknot following the slippery site promotes a ribosomal pause (Tu, C., Tzeng, T.-H. and Bruenn, J. A. (1 992);Somogyi, P., Jenner, A. J., Brierley, I. A. and Inglis, S. C. (1993)). The paused ribosome may also trigger assembly of the surveillance complex. This complex, or a subset of the Upf proteins, may help the ribosome to maintain the appropriate translational reading frame. In the absence of the these factors the ribosome is more prone to slip and change reading frame.

REFERENCES

Altamura, N., Groudinsky, O., Dujardin, G. and Slonimski, P. P. (1992) NAM7 nuclear gene encodes a novel member of a family of helicases with a Z1-6n-ligand motif and is involved in mitochondrial functions in Saccharomyces cerevisiae. J. Mol. Biol. 224, 575–587.

Andjelkovic, N., Zolnierowicz, S., Van Hoof, C., Goris, J., and Hemmings, B. A. (1996) The catalytic subunit of protein phosphatase 2A associates with the translation termination factor eRF1. EMBO J. 15, 7156–67.

Applequist, S. E., Selg, M., Roman C., and Jack, H. M. (1997) Cloning and characterization of HUPF1, a human homologue of the Saccharomyces cerevisiae nonsense mRNA-reducing UPF1 protein. Nucleic Acids Res. 25, 814–821.

Atkin A. L., Altamura, N. Leeds, P., and Culbertson, M. R. (1995) The majority of yeast UPF1 co-localizes with polyribosomes in the cytoplasm. Mol. Biol. Cell 6, 611–625.

Atkin, A. L., Schenkman, L. R., Eastham, M., Dahlseid, J. N., Lelivelt, M. J., Culbertson, M. R. (1997) Relationship between yeast polyribosomes and Upf proteins required for nonsense mediated mRNA decay. J. Biol. Chem. 272, 22163–22172.

Beelman, CA and Parker, R. (1995) mRNA degradation in eukaryotes. Cell 81, 179–183.

Belgrader, P, Cheng, J. and Maquat, L. E. (1993) Evidence to implicate translation by ribosomes in the mechanism by which nonsense codons reduce the nuclear level of human triosephosphate isomerase mRNA. Proc. Nat'l. Acad. Sci. USA. 90: 482–486.

Brierley, I. (1995) J. Gen. Virol. 76, 1885–1892.

Buckingham, R., Grentzmann, G., and Kisselev, L. (1997) Polypeptide chain release factors. Mol. Microbiol. 24. 449–456.

Caponigro, G. and Parker, R. (1996) Mechanisms and control of mRNA turnover in Saccharomyces cerevisiae. Microbiol. Rev. 60, 233–249.

Cui, Y., Hagan, K. W., Zhang S., and Peltz, S. W. (1995) Identification and characterization of genes that are required for the accelerated degradation of mRNAs containing a premature translational termination codon. Genes & Dev. 9, 423–436.

Cui, Y., Dinman, J. D. D., Goss Kinzy, T. and Peltz, S. W. 1997 The mof2/Sui1 protein is a general monitor of translational accuracy. Mol. Cell. Biol. in press Cui, Y., Dinman, J. D., and Peltz, S. W. (1996) mof4-1 is an allele of the UPF1/IFS2 gene which affects both mRNA turnover and −1 ribosomal frameshifting efficiency. EMBO J. 15, 5726–5736.

Czaplinski, K., Weng, Y., Hagan, K. W. and Peltz, S. W. (1995) Purification and characterization of the Upf1p: a factor involved in translation and mRNA degradation. RNA 1, 610–623.

Didichenko, S. A., Ter-Avanesyan, M. D., and Smirnov, V. N. (1991) EF-1a-like ribosome-bound protein of yeast Saccharomyces cerevisiae. Eur. J. Biochem. 198, 705–711.

Dietz, H. C., I. McIntosh, L. Y. Sakai, G. M. Corson, S. C. Chalberg, R. E. Pyeritz, and Francomano, C. A. (1993) Four novel FBN1 mutations: significance for mutant transcript level and EGF-like domain calcium binding in the pathogenesis of Marfan syndrome. Genomics 17, 469–475.

Dietz. H. C., U. Franke, H. Furthmayr. C. A. Francomano, A. De Paepe, R. Devereux, F. Ramirez, and Pyeritz, R. E. (1995) The question of heterogeneity in Marfan syndrome. Nature Genetics 9, 228–231.

Dinman, J. D. and Wickner, R. B. (1994) Translational maintenance of frame: mutants of *Saccharomyces cerevisiae* with altered −1 ribosomal frameshifting efficiencies. *Genetics* 136, 75–86.

Dinman, J. D. (1995). Ribosomal frameshifting in yeast viruses. *Yeast*, 11, 1115–1127.

Dinman, J. D., and Wickner, R. B. (1992) Ribosomal frameshifting efficiency and gag/gag-pol ratio are critical for yeast $M_1$ double-stranded RNA virus propagation. *J. Virol.* 66, 3669–3676.

Dinman, J. D., Icho, T., and Wickner, R. B. (1991) A −1 ribosomal frameshifting in a double-stranded RNA virus of yeast forms a Gag-pol fusion protein. *Proc. Natl. Acad. Sci. USA* 88, 174–178.

Dinman, J. D., Ruiz-Echevarria, M. J. Czaplinski, K. and Peltz, S. W. (1997b) Peptidyl-transferase inhibitors have antiviral properties by altering programmed −1 ribosomal frameshifting efficiencies: development of model systems. *Proc. Natl. Acad. Sci. USA* 94, 6606–6611.

Dinrnan, J. D. D., Ruiz-Echevarria, M. J. and Peltz, S. W. (1997) Translating old drugs into new treatments: ribosomal frameshift as a target for antiviral agents. *Tibtech*. in press.

Farabaugh, P. J. (1995). Post-transcriptional regulation by Ty retrotransposon of *Saccharomyces cerevisiae*. *J. Biol. Chem.* 270, 10361–10364.

Ferguson. J. J., Groppe, J. C. and Reed, S. I. (1981) Construction and characterization of three yeast-*Escherichia coli* shuttle vectors designed for rapid subcloning of yeast genes on small DNA fragments. *Gene* 16, 191–197.

Frolova, L., Le Goff, X., Rasmussen, H. H., Cheperegin, S.,Drugeon, G., Kress, M., Arman, I., Haenni, A. L., Celis, L. E., Phillippe, M., Justesen, J., and Kisselev, L. (1994) A highly conserved eukaryotic protein family possessing properties of a polypeptide chain release factor. *Nature* 372, 701–703.

Frolova, L., Le Goff X., Zhouravleva, G., Davydova, E., Philippe, M. and Kisselev, L. (1996) Eukaryotic polypeptide, chain release factor eRF3 is an eRF1- and ribosome-dependent guanosine triphosphatase. *RNA* 4, 334–341.

Glover J. R., Kowal, A. S., Schirmer, E. C., Patino, M. M., Liu J. J. and Lindquist S. (1997) Self-seeded fibers formed by Sup35, the protein determinant of [PSI+], a heritable prion-like factor of *S. cerevisiae*. *Cell* 89, 811–819.

Gottesman S., R. Wickner, and M. R. Maurizi. (1997). Protein quality control: triage by chaperones and proteases. *Genes & Dev.* 11, 815–823.

Gozalbo, D. and Hohmann, S. (1990) Nonsense suppressors partially revert the decrease of the mRNA levels of a nonsense mutant allele in yeast. *Curr. Genetics* 17, 77–79.

Guarente, L. (1983) Yeast promoters and LacZ fusions designed to study expression of cloned genes in yeast. *Methods in enzymol.* 101, 181–191.

Hagan, K. W., Ruiz-Echevarria, M. J., Quan, Y. and Peltz S. W. (1995) Characterization of cis-acting sequences and decay intermediates involved in nonsense-mediated mRNA turnover. *Mol. Cell. Biol.* 15, 809–823.

Hall, G. W., and Thein, S. (1994) Nonsense-codons mutations in the internal exon of the β-globin gene are not associated with a reduction in β-mRNA accumulation: A mechanism for the phenotype of dominant β-thalassemia. *Blood* 83, 2031–2037.

Hayashi, S.-I., and Murakami, Y. (1995) Rapid and regulated degradation of ornithine decarboxylase. Biochem. J. 306, −10.

He, F., Brown, A. H., and Jacobson, A. (1997) Upf1p, Nmd2p, and Upf3p are interacting components of the yeast nonsense-mediated mRNA decay pathway. *Mol. Cell. Biol.* 17, 1580–94.

He, F. and Jacobson A. (1995) Identification of a novel component of the nonsense-mediated mRNA decay pathway using an interacting protein screen. Genes & Dev. 9, 4437–454.

He, F., Peltz, S. W., Donahue, J. L., Rosbash, M. and Jacobson, A. (1993) Stabilization and ribosome association of unspliced pre-mRNAs in a yeast upf1- mutant. *Proc. Natl. Acad. Sci. USA* 90, 7034–7038.

Howard, M., Frizzell R. A and Bedwell D. M. (1996) Aminoglycoside antibiotics restore CFTR function by overcoming premature stop mutations. *Nature Med.* 2,467–9

Jacobson, A. (1996). Poly(A) metabolism and translation: the closed loop model. In *Translational control* (eds. Hershey, J. W. B. Mathews, M. B. and Sonenberg N.) Cold Spring Harbor Laboratory Press, Plainview N.Y. 451–480.

Jacobson, A. and Peltz, S. W. (1996) Interrelationships of the pathways of mRNA decay and translation in eukaryotic cells. *Ann. Rev. Biochem.* 65, 693–739.

Koonin, E. V. (1992). A new group of putative RNA helicases. *TIBS* 17, 495–497.

Lee, B. S., and Culbertson, M. R. (1995) Identification of an additional gene required for eukaryotic nonsense mRNA turnover. *Proc. Natl. Acad. Sci. USA* 92, 10354–10358.

Leeds, P., Peltz, S. W., Jacobson, A. and Culbertson, M. R. (1991) The product of the yeast UPF1 gene is required for rapid turnover of mRNAs containing a premature translational termination codon. *Genes & Dev.* 5, 2303–2314.

Leeds, P., Wood, J. M., Lee, B. S. and Culbertson, M. R. (1992) Gene products that promote mRNA turnover in *Saccharomyces cerevisiae*. *Mol. Cell. Biol.* 12, 2165–2177.

Long, R. M., Elliot, D. J., Stutz, F., Rosbash. M., and Singer, R. H. (1995) Spatial consequences of defective processing of specific yeast mRNAs revealed by fluorescent in situ hybridization. *RNA* 1, 1071–1078.

Losson R., and Lacroute, F. (1979) Interference of nonsense mutations with eukaryotic messenger RNA stability. *Proc. Natl. Acad. Sci. USA* 76, 5134–7.

Maquat, L. E. (1995) When cells stop making sense: effects of nonsense codons on RNA metabolism in vertebrate cells. *RNA* 1, 453–465.

McKusick, V. A.; (with the assistance of Francomano, C. A., Antonarakis, S. E., and Pearson, P. L. (1994) Mendelian inheritance in man : a catalog of human genes and genetic disorders Johns Hopkins University Press. Baltimore Md. (Web site-http://www.ncbi.nlm.nih.gov/Omim/).

Muhlrad D. and Parker, R. (1994) Premature translational termination triggers mRNA decapping. *Nature* 370, 578–581.

Patino, M. M., Liu, J. J., Glover J. R. and Lindquist, L. (1996) Support for the prion hypothesis for inheritance of a phenotypic trait in yeast. *Science* 273, 622–626.

Paushkin S. V., Kushnirov, V. V., Smimov, V. N. and Ter-Avanesyan, M. D. (1996) Propagation of the yeast prion-like [PSI+] determinants mediated by oligomerization of the Sup35-encoded polypeptide chain-release factor. *EMBO J.* 15, 317–3134.

Paushkin S. V., Kushnirov, V. V., Smirnov, V. N. and Ter-Avanesyan, M. D. (1997a). In Vitro propagation of the prion-like state of yeast Sup35 protein. *Science* 277, 381–383.

Paushkin S. V., Kushnirov, V. V., Smirnov, V. N. and Ter-Avanesyan, M. D. (1997b). Interaction between yeast Sup45p(eRF1) and Sup35p(eRF3) polypeptide chain release factors: Implications for prion-dependent regulation. *Mol. Cell. Biol.* 17, 2798–2805.

Peltz, S. W., Brown, A. H. and Jacobson, A. (1993) mRNA destabilization triggered by premature translational termination depends on three mRNA sequence elements and at least one trans-acting factor. *Genes & Dev.* 7, 1737–1754.

Peltz, S. W., Trotta. C., Feng, H., Brown, A. H., Donahue, J. L., Welch, E. W. and Jacobson, A. (1993a) Identification of the cis-acting sequences and trans-acting factors involved in nonsense-mediated mRNA decay. In *Protein Synthesis and Targeting in Yeast* (Eds. M. Tuite, J. McCarthy, A. Brown, and F. Sherman), Springer-Verlag H71:1–10.

Peltz, S. W., Feng, H., Welch, E. W. and Jacobson, A. (1994) Nonsense-mediated mRNA decay in yeast. In *Progress in Nucleic Acid Research and Molecular Biology*. Vol 47. pp. 271–298. Academic press, New York.

Perlick, H. A., Medghalchi, S. M., Spencer, F. A., Kendzior, R. J. Jr. and Dietz, H. C. (1996) Mammalian orthologues of a yeast regulator of nonsense-transcript stability. *Proc. Natl. Acad. Sci. USA* 93, 10928–10932.

Pulak, R. and Anderson, P. (1993) mRNA surveillance by the *Caenorhabditis elegans* smg genes. *Genes & Dev.* 7, 1885–1897.

Rose, M. D., Winston, D. F. and Hieter, P. (1990) Methods in Yeast Genetics. Cold Spring harbor Laboratory Press, Cold Spring Harbor, N.Y.

Ross, J. (1995) mRNA stability in mammalian cells. *Microbiol. Rev.* 59, 423–450.

Ruiz-Echevarria, M. J., K. Czaplinski, and S. W. Peltz. (1996) Making sense of nonsense in yeast. *TIBS* 21, 433–438.

Ruiz-Echevarria, M. J., Gonzalez, C. I. and Peltz. S. W. (1998) Identifying the right stop: Determining how the surveillance complex recognizes and degrades an aberrant mRNA. *EMBO J.* 17, 575–589.

Ruiz-Echevarria, M. J., and Peltz, S. W. (1996). Utilizing the GCN4 leader region to investigate. the role of the sequence determinants in nonsense-mediated mRNA decay. *EMBO J.* 15, 2810–2819.

Scheistl, R. H. and Geitz, R. D. (1989) High efficiency transformation of intact yeast cells using single stranded nucleic acids as a carrier. *Curr. Genetics* 16: 339–346. 40.

Somogyi, P., Jenner, A. J., Brierley, I. A. and Inglis, S. C. (1993) Ribosomal pausing during translation of an RNA pseudoknot. *Mol. Cell Biol.* 13, 6931–6940.

Stansfield, I., Grant C. M.,Akhmaloka, and Tuite, M. F. (1992) Ribosomal association of the yeast SAL4(SUP45) gene product: implications for its role in translation fidelity and termination. *Mol. Microbiol.* 6, 3469–3478.

Stansfield, I., Jones, K. M., Kushnirov, V. V., Dagakesarnanskaya, A. R., Poznyakov, A. I., Paushkin, S. V., Nierras. C.R. Cox, B. S., Ter-Avanesyan, M. D. and Tuite, M. F. (1995) The products of the SUP45(eRF1) and SUP35 genes interact to mediate translation termination in *Saccharomyces cerevisiae*. *EMBO J.* 14, 4365–4373.

Suzuki, C. K., Rep, M., van Dijl, J. M., Suda, K., Grivell, L. A. and Schatz, G. (1997) ATP-dependent proteases that also chaperone protein biogenesis. *TIBS* 22, 118–123.

Tarun, S. Z., Wells, S. E., Deardorff, J. A. and Sachs, A. B. (1997) Translation initiation factor eIF4G mediates in vitro poly(A) tail-dependent translation. *Proc. Natl. Acad. Sci. USA*. 94, 9046–9051.

Ter-Avanesan, M. D., Dagkesamanskaya, A. R., Kushnirov, V. V. and Smirnov, V. N. (1994) The SUP35 omnipotent suppressor is involved in the maintenance of the non-Mendelian determinant [PSI$^+$] in the yeast *Saccharomyces cerevisiae*. *Genetics* 137, 671–676.

Tu, C., Tzeng, T.-H. and Bruenn, J. A. (1992). Ribosomal movement impeded at a pseudoknot required for ribosomal frameshifting. *Proc. Natl. Acad. Sci USA* 89, 8636–8640.

Tate, W. P. and Brown, C. M. (1992) Translation termination: "Stop" for protein synthesis or "Pause" for regulation of gene expression. *Biochemistry* 31, 2443–2450.

Weng, Y., Czaplinski, K. and Peltz, S. W. (1996a) Genetic and biochemical characterization of the mutations in the ATPase and helicase regions of Upf1 Protein. *Mol. Cell. Biol.* 16, 5477–5490.

Weng, Y., Czaplinski, K. and Peltz, S. W. (1996b) Identification and characterization of mutations in the UPF1 gene that affect nonsense suppression and the formation of the Upf protein complex, but not mRNA turnover. *Mol. Cell. Biol.* 16, 5491–5506.

Weng, Y., Czaplinski, K. and Peltz, S. W. (1998) ATP is a cofactor of the Upf1 protein that modulates it translation termination and RNA binding activities. *RNA* 4, 205–214.

Weng, Y., Ruiz-Echevarria, M. J., Zhang, S., Cui, Y., Czaplinski, K., Dinman J. D. and Peltz, S. W. (1997) Characterization of the nonsense-mediated mRNA decay pathway and its effect on modulating translation termination and programmed frameshifting. In: *mRNA Metabolism and Post-transcriptional Gene Regulation*. Modern Cell Biology 17, 241–263.

Wickens, M., Anderson, P. and Jackson, R. J. (1997) Life and death in the cytoplasm: messages from the 3' end. *Curr. Opin. Genet. & Dev.* 7, 220–32.

Wickner. R. B. (1994) [URE3] as an altered URE2 protein: evidence for a prion analog in *Saccharomyces cerevisiae*. *Science* 264, 566–569.

Wolin, S. L. and Walter, P. (1988) Ribosome pausing and stacking during translation of a eukaryotic mRNA. *EMBO J.* 7, 3559–3569.

Zhang, J. and Maquat, L. E. (1997) Evidence that translation reinitiation abrogates nonsense-mediated mRNA decay in mammalian cells. *EMBO J.* 16, 826–833.

Zhang, S., Ruiz-Echevarria, M. J., Quan Y. and Peltz S. W. (1995) Identification and characterization of a sequence motif involved in nonsense-mediated mRNA decay. *Mol. Cell. Biol.* 15, 2231–2244.

Zhang, S., Welch, E. W., Hagan, K. W., Brown, A. H., Peltz, S. W. and Jacobson, A. (1995) Polysome associated mRNAs are substrates for the nonsense mediated mRNA decay pathway in *Saccharomyces cerevisiae*. *RNA* 3, 234–244.

Zhouravleva, G, Frolova, L., LeGoff, X., LeGuellec, R., Inge-Vechtomov, S., Kisselev, L. and Phillippe, M. (1995) Termination of translation in eukaryotes is governed by two interacting polypeptide chain release factors, eRF1 and eRF3. *EMBO J.* 14, 4065–4072.

What is claimed is:

1. An isolated multiprotein complex comprising a human Upf1p protein, a peptidyl eucaryotic release factor 1 (eRF1) and a peptidyl eucaryotic release factor 3 (eRF3), wherein the complex is effective to modulate peptidyl transferase activity during translation.

2. The complex of claim 1, further comprising human Upf3p and Upf2p.

3. The complex of claim 1, further comprising human Upf3p or Upf2p.

* * * * *